United States Patent
Borchardt et al.

(10) Patent No.: US 9,050,783 B2
(45) Date of Patent: *Jun. 9, 2015

(54) MULTI-LAYERED BAGS WITH SHORTENED INNER LAYER

(75) Inventors: Michael G. Borchardt, Naperville, IL (US); Kyle R. Wilcoxen, Chicago, IL (US); Robert W. Fraser, Lombard, IL (US); Robert T. Dorsey, Western Springs, IL (US); Shaun T. Broering, Fort Thomas, KY (US); Jack A. MacPherson, Aurora, IL (US); Scott Binger, Bridgeview, IL (US); Ken Cisek, Chicago, IL (US); Theodore J. Fish, Downers Grove, IL (US)

(73) Assignee: The Glad Products Company, Oakland, CA (US)

( * ) Notice: Subject to any disclaimer, the term of this patent is extended or adjusted under 35 U.S.C. 154(b) by 156 days.

This patent is subject to a terminal disclaimer.

(21) Appl. No.: 13/412,940

(22) Filed: Mar. 6, 2012

(65) Prior Publication Data

US 2012/0163738 A1    Jun. 28, 2012

Related U.S. Application Data

(63) Continuation-in-part of application No. 13/273,384, filed on Oct. 14, 2011, now Pat. No. 8,888,365, which is a continuation-in-part of application No. 12/947,025, filed on Nov. 16, 2010, now Pat. No. 8,603,609.

(60) Provisional application No. 61/261,673, filed on Nov. 16, 2009.

(51) Int. Cl.
*B65D 30/08* (2006.01)
*B65D 33/00* (2006.01)
(Continued)

(52) U.S. Cl.
CPC ............... *B32B 27/306* (2013.01); *A61F 7/08* (2013.01); *B31B 37/00* (2013.01); *B65D 31/02* (2013.01); *B32B 27/36* (2013.01); *B32B 27/308* (2013.01); *B32B 27/32* (2013.01); *B32B 2439/06* (2013.01)

(58) Field of Classification Search
CPC ............ B31B 37/00; B65D 31/02; A61F 7/08
USPC ................ 383/37, 109, 75, 105, 38, 111, 112
See application file for complete search history.

(56) References Cited

U.S. PATENT DOCUMENTS 2,898,027 A  *  8/1959  Scholle .................... 229/117.33
3,008,862 A     11/1961  Haine et al.
(Continued)

FOREIGN PATENT DOCUMENTS

| JP | 2001199451 A | * | 7/2001 | ............. B65D 30/08 |
| JP | 2002284250 A | * | 10/2002 | ............. B65D 81/28 |
| WO | WO97/29966 | | 8/1997 | |

OTHER PUBLICATIONS

International Search Report, mailed May 6, 2013, from counterpart PCT/US 13/28882, filing date Mar. 4, 2013.

*Primary Examiner* — Jes F Pascua
(74) *Attorney, Agent, or Firm* — Thomas C. Feix

(57) ABSTRACT

Multi-layered bags include an outer layer or bag and an inner layer or bag that is shorter than the outer layer or bag. The shortened inner layer or bag can stretch or expand to the outer layer or bag when loaded with objects or otherwise strained. Such multi-layered bags can allow for a reduction in thermoplastic material without compromising the strength of the multi-layered bag. In various implementations, the inner layer or bag may be non-continuously laminated, continuously laminated, or joined only along one or more edges to the outer layer or bag. Implementations including non-continuous bonds securing the inner layer or bag to the outer layer or bag can provide additional strength to the bag. Methods of forming multi-layered bags with a shortened inner layer including inserting an inner layer within an outer layer and then joining the layers to form a bag.

20 Claims, 9 Drawing Sheets

(51) Int. Cl.
　　*B32B 27/30* (2006.01)
　　*A61F 7/08* (2006.01)
　　*B31B 37/00* (2006.01)
　　*B32B 27/36* (2006.01)
　　*B32B 27/32* (2006.01)

(56) References Cited

U.S. PATENT DOCUMENTS

| | | | |
|---|---|---|---|
| 3,319,539 A * | 5/1967 | Johnson et al. | 493/381 |
| 3,494,457 A | 2/1970 | Titchenal | |
| 3,592,379 A * | 7/1971 | Nakamura | 383/6 |
| 3,734,394 A * | 5/1973 | Dooley | 383/109 |
| 3,772,968 A * | 11/1973 | Ruda | 493/225 |
| 4,273,549 A | 6/1981 | Pezzana et al. | |
| 4,629,064 A | 12/1986 | Barner | |
| 4,755,064 A * | 7/1988 | Weber | 383/110 |
| 4,846,586 A | 7/1989 | Bruno | |
| 4,854,736 A * | 8/1989 | McVeigh | 383/76 |
| 4,890,936 A | 1/1990 | Cooper | |
| 4,925,711 A | 5/1990 | Akao et al. | |
| 4,993,844 A | 2/1991 | Robinson et al. | |
| 5,501,525 A * | 3/1996 | Cox et al. | 383/103 |
| 5,716,137 A | 2/1998 | Meyer | |
| 5,804,265 A * | 9/1998 | Saad et al. | 428/35.2 |
| 5,881,883 A | 3/1999 | Siegelman | |
| 5,958,483 A * | 9/1999 | Anders et al. | 426/112 |
| 6,371,643 B2 * | 4/2002 | Saad et al. | 383/63 |
| 6,416,452 B1 | 7/2002 | Meyer | |
| 6,550,966 B1 * | 4/2003 | Saad et al. | 383/103 |
| 6,579,008 B2 | 6/2003 | Price et al. | |
| 7,132,151 B2 * | 11/2006 | Rasmussen | 428/182 |
| 7,270,861 B2 * | 9/2007 | Broering et al. | 428/35.7 |
| 7,569,263 B2 * | 8/2009 | Hanaichi et al. | 428/35.4 |
| 7,631,762 B2 * | 12/2009 | Liao et al. | 206/522 |
| 2001/0043673 A1 | 11/2001 | Gershon | |
| 2004/0179754 A1 | 9/2004 | Taheri | |
| 2004/0247806 A1 | 12/2004 | Schmal | |
| 2006/0093766 A1 * | 5/2006 | Savicki et al. | 428/35.2 |
| 2009/0230132 A1 | 9/2009 | Takedutsumi et al. | |
| 2010/0086242 A1 * | 4/2010 | Morizane | 383/75 |
| 2011/0117307 A1 * | 5/2011 | Fraser et al. | 428/66.6 |
| 2012/0033900 A1 * | 2/2012 | Fraser et al. | 383/105 |
| 2012/0039550 A1 * | 2/2012 | Macpherson et al. | 383/109 |
| 2012/0057811 A1 * | 3/2012 | Tucker et al. | 383/72 |
| 2012/0063704 A1 * | 3/2012 | Hoying et al. | 383/75 |
| 2012/0063706 A1 * | 3/2012 | Fraser et al. | 383/109 |
| 2013/0188889 A1 * | 7/2013 | Fraser et al. | 383/37 |

* cited by examiner

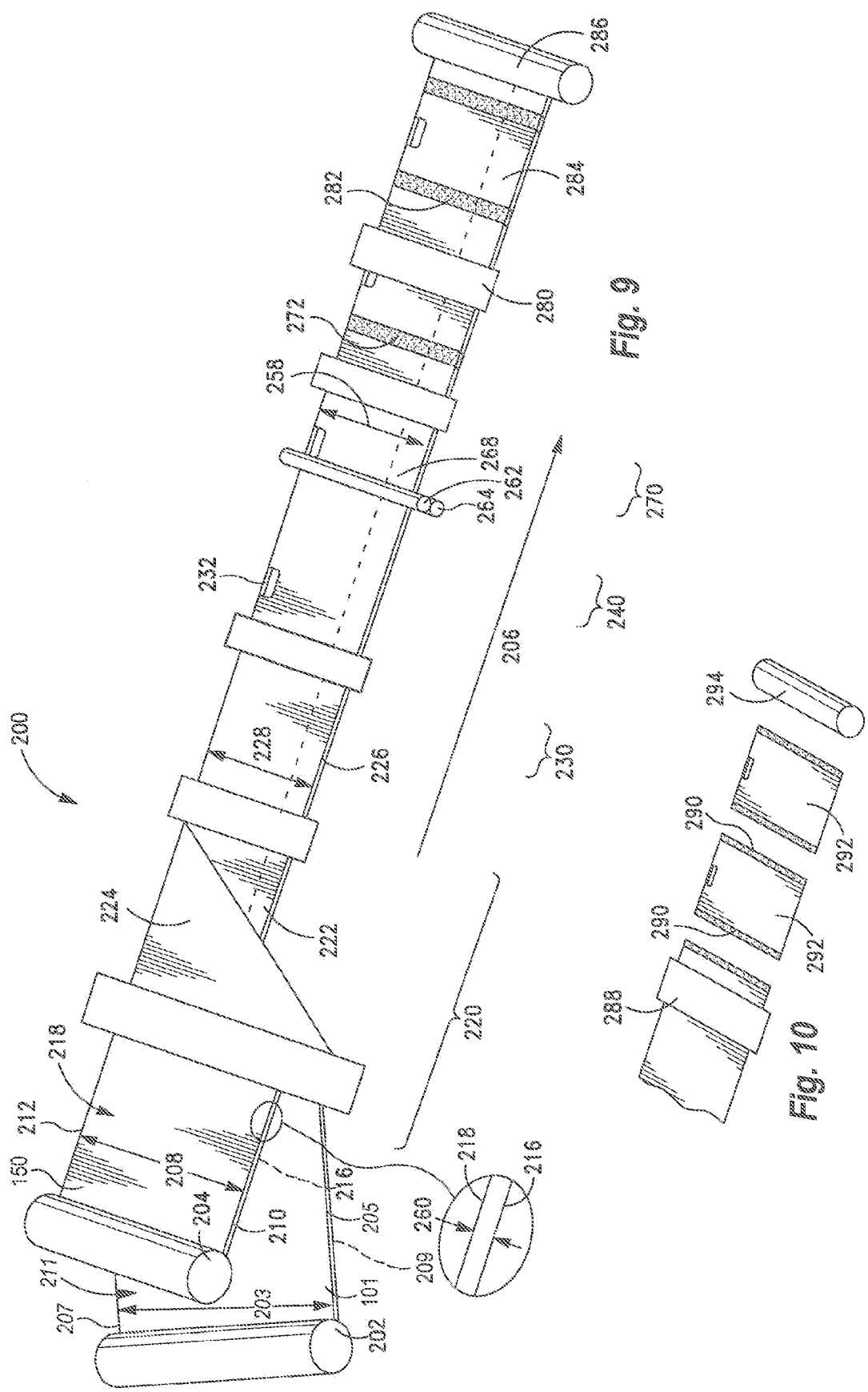

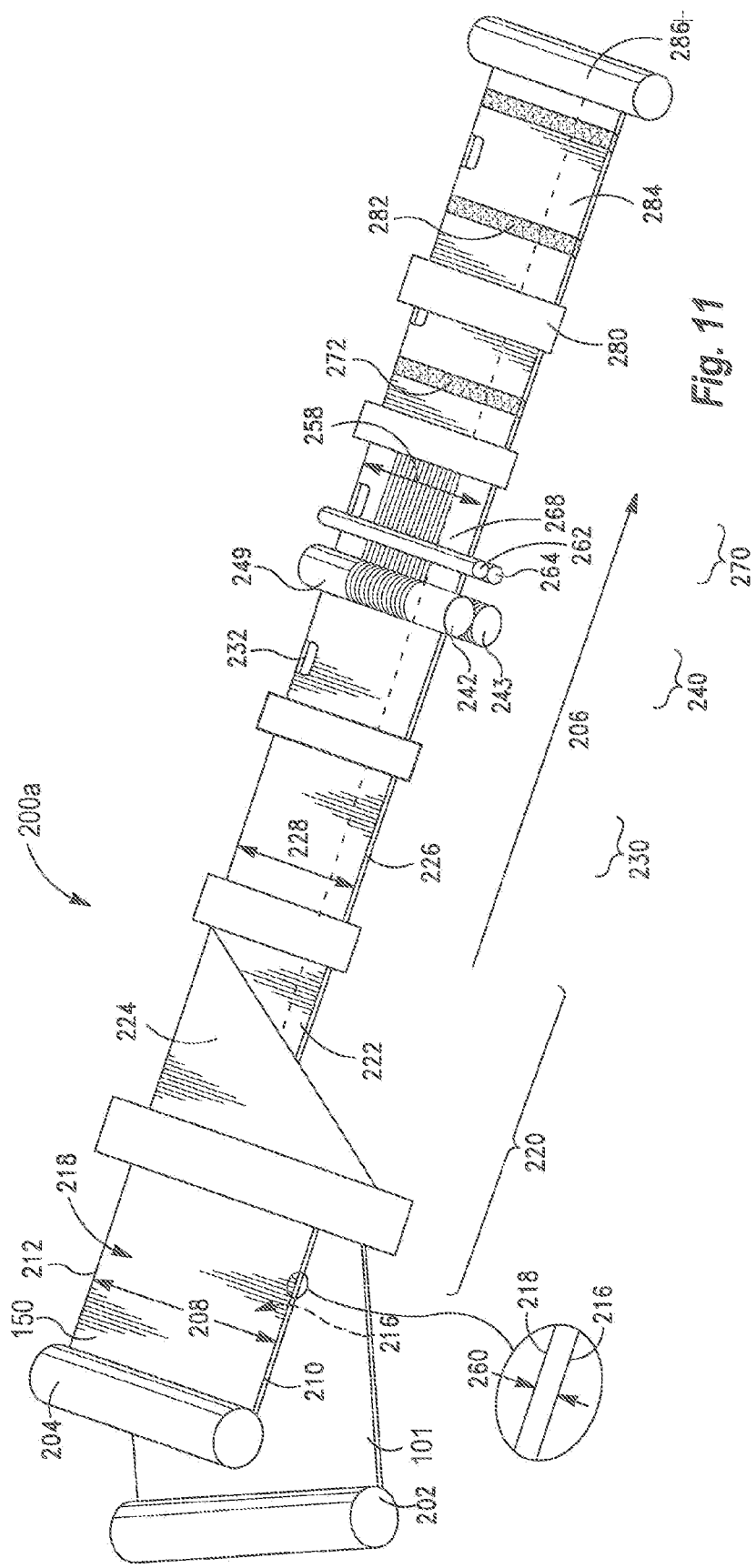

MULTI-LAYERED BAGS WITH SHORTENED INNER LAYER

CROSS-REFERENCE TO RELATED APPLICATIONS

The present application is a continuation in part of U.S. patent application Ser. No. 13/273,384 filed Oct. 14, 2011 and entitled NON-CONTINUOUSLY LAMINATED MULTI-LAYERED BAGS, now U.S. Pat. No. 8,888,365, which is a continuation in part of U.S. patent application Ser. No. 12/947,025 filed Nov. 16, 2010 and entitled DISCONTINUOUSLY LAMINATED FILM, now U.S. Pat. No. 8,603,609, which claims the benefit of U.S. Provisional Application No. 61/261,673, filed Nov. 16, 2009. Each of the above-referenced applications is hereby incorporated by reference in its entirety.

BACKGROUND OF THE INVENTION

1. The Field of the Invention

The present invention relates generally to thermoplastic films and bags formed therefrom.

2. Background and Relevant Art

Thermoplastic films are a common component in various commercial and consumer products. For example, grocery bags, trash bags, sacks, and packaging materials are products that are commonly made from thermoplastic films. Additionally, feminine hygiene products, baby diapers, adult incontinence products, and many other products include thermoplastic films to one extent or another.

The cost to produce products including thermoplastic film is directly related to the cost of the thermoplastic film. Recently the cost of thermoplastic materials has risen. In response, many manufacturers attempt to control manufacturing costs by decreasing the amount of thermoplastic material in a given product.

One way manufacturers may attempt to reduce production costs is to use thinner films or stretch the thermoplastic films, thereby increasing surface area and reducing the amount of thermoplastic film needed to produce a product of a given size. Unfortunately, stretched or otherwise thinner thermoplastic films can have undesirable properties. For example, thinner thermoplastic films are typically more transparent or translucent. Additionally, consumers commonly associate thinner films with weakness. Such consumers may feel that they are receiving less value for their money when purchasing products with thinner films; and thus, may be dissuaded to purchase thinner thermoplastic films. As such, manufacturers may be dissuaded to stretch a film or use thinner films despite the potential material savings.

Accordingly, there are a number of considerations to be made in thermoplastic films and manufacturing methods.

BRIEF SUMMARY OF THE INVENTION

Implementations of the present invention solve one or more problems in the art with apparatus and methods for creating multi-layered bags with an inner bag that is shorter than the outer bag. The shortened inner bag can absorb forces and stretch to the size of the outer bag before the outer bag is significantly strained. Once stretched the inner bag can work in concert with the outer bag(s) to provide strength. Such implementations can provide an overall bag employing a reduced amount of raw material that nonetheless has maintained or increased strength parameters. Alternatively, such implementations can use a given amount of raw material and provide a bag with increased strength parameters.

For example, one implementation of a multi-layered thermoplastic bag with a shortened inner layer includes a first thermoplastic bag and a second thermoplastic bag positioned within the first thermoplastic bag. Each of the first and second thermoplastic bags include first and second opposing sidewalls joined together along a first side edge, an opposite second side edge, and a bottom edge. At least a portion of the respective top edges of the first and second sidewalls and the third and fourth sidewalls are un-joined to define an opening. Additionally, the second thermoplastic bag is shorter than the first thermoplastic bag such that the bottom edge of the second thermoplastic bag is spaced a distance from the bottom edge of the first thermoplastic bag.

Another implementation of the present invention includes a multi-layered bag comprising a first sidewall comprising a first layer of a thermoplastic material and an adjacent second layer of thermoplastic material. The multi-layered bag also includes a second sidewall comprising a first layer of a thermoplastic material and an adjacent second layer of thermoplastic material. The first layers of the first and second sidewalls each have a first length. The second layers of the first and second sidewalls each have a second length that is less than the first length. The second sidewall is joined to the first sidewall along a first side edge, an opposing second side edge, and a bottom edge. Furthermore, at least a portion of respective top edges of the first and second sidewalls define an opening of the multi-layered bag.

In addition to the forgoing, a method for forming a multi-layered thermoplastic bag within a shortened inner layer involves providing a first thermoplastic film having a first width. The method also involves providing a second thermoplastic film having a second width, the second width being smaller than the first width. Additionally, the method involves folding the first and second thermoplastic films in half along their widths. The method also involves joining at least two edges of the first thermoplastic film together to form a bag configuration. Similarly, the method involves joining at least two edges of the second thermoplastic film together to form a bag configuration. The method further involves joining the first and second thermoplastic films together.

Additional features and advantages of exemplary embodiments of the present invention will be set forth in the description which follows, and in part will be obvious from the description, or may be learned by the practice of such exemplary embodiments. The features and advantages of such embodiments may be realized and obtained by means of the instruments and combinations particularly pointed out in the appended claims. These and other features will become more fully apparent from the following description and appended claims, or may be learned by the practice of such exemplary embodiments as set forth hereinafter.

BRIEF DESCRIPTION OF THE DRAWINGS

In order to describe the manner in which the above-recited and other advantages and features of the invention can be obtained, a more particular description of the invention briefly described above will be rendered by reference to specific embodiments thereof which are illustrated in the appended drawings. It should be noted that the figures are not drawn to scale, and that elements of similar structure or function are generally represented by like reference numerals for illustrative purposes throughout the figures. Understanding that these drawings depict only typical embodiments of the invention and are not therefore to be considered to be limiting of its scope, the invention will be described and explained with additional specificity and detail through the use of the accompanying drawings in which:

FIG. 9 illustrates a schematic view depicting a high-speed manufacturing process for producing multi-layered thermoplastic bags having shortened inner layers in accordance with one or more implementations of the present invention;

FIG. 10 illustrates a schematic view of the final steps of one or more implementations of the high-speed manufacturing process shown in FIG. 9;

FIG. 11 illustrates a schematic view of another high-speed manufacturing process for producing multi-layered thermoplastic bags having shortened inner layers in accordance with one or more implementations of the present invention.

DETAILED DESCRIPTION

Figure 1:
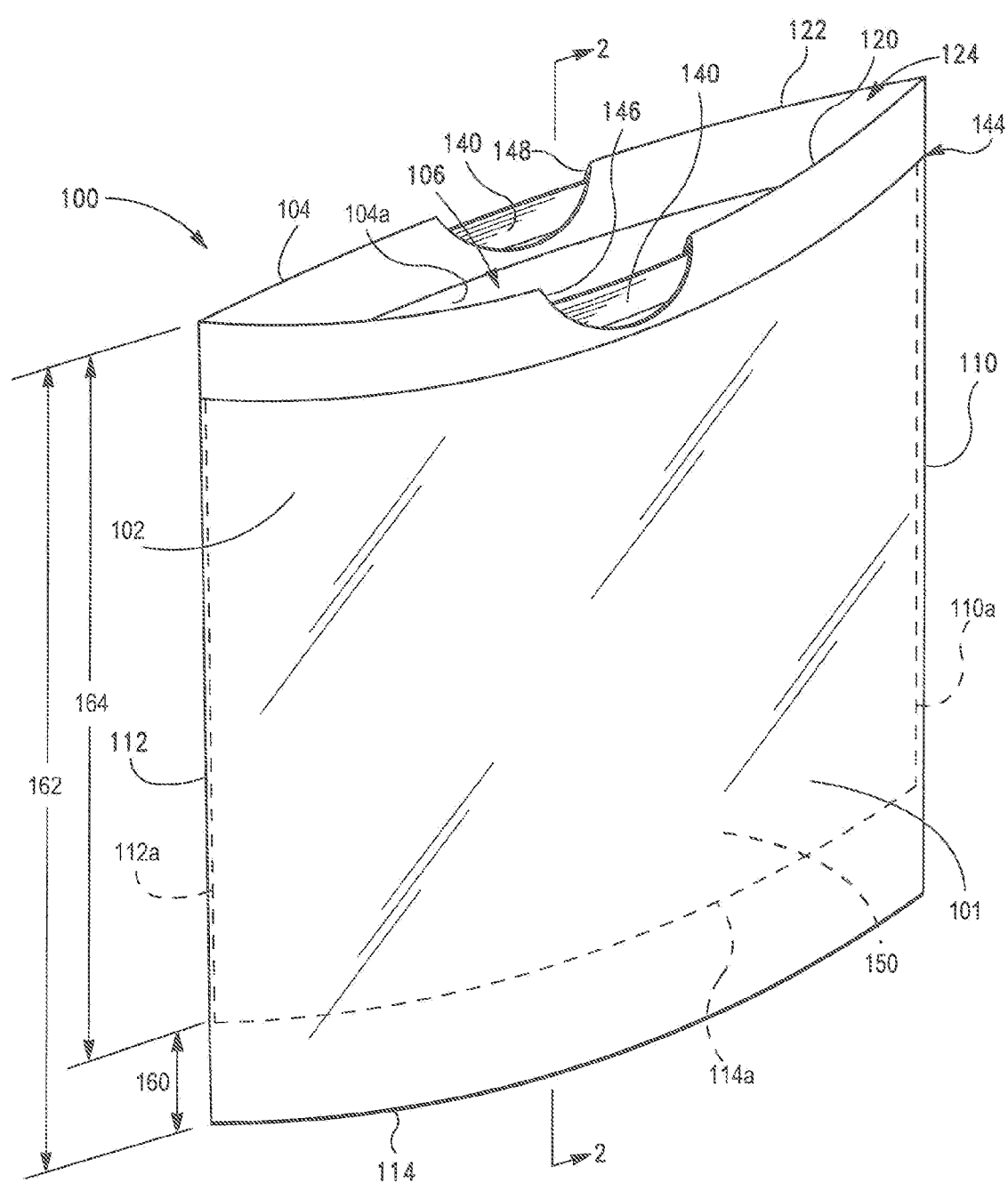
FIG. 1 illustrates a perspective view of a multi-layered thermoplastic bag with a shortened inner layer in accordance with one or more implementations of the present invention.

One or more implementations of the present invention include apparatus and methods for creating multi-layered bags with an inner bag that is shorter than the outer bag. The shortened inner bag can absorb forces and stretch to the size of the outer bag(s) before the outer bag(s) is significantly strained. Once stretched the inner bag can work in concert with the outer bag(s) to provide strength. Such implementations can provide an overall bag employing a reduced amount of raw material that nonetheless has maintained or increased strength parameters. Alternatively, such implementations can use a given amount of raw material and provide a bag with increased strength parameters.

For example, in one or more implementations the combined layers of the multi-layered bag may use less material than a conventional bag, but nonetheless have maintained or increased strength parameters provided by the layers of the bag working in concert with each other. In particular, in one or more implementations the layers of the multi-layered bag are thinner and/or stretched to reduce the amount of thermoplastic material to form a bag of a given size. For instance, one or more layers of the multi-layered bag can be continuously stretched or incrementally stretched to thin the layer and/or increase or otherwise modify the strength parameters of the layers. Suitable stretching methods include machine direction orientation ("MDO"), ring rolling, a structural elastic like film (SELF) process, embossing, or other methods.

As the multi-layered bags of the present invention include two or more layers, the layers can be provided with different aesthetic, material, or strength properties. For example, in one or more implementations the inner layer of the multi-layered bag can include elastic characteristics that allow the inner layer to stretch to the outer layer(s). The inner layer can include elastic characteristics either by material choice or processing (e.g., SELFing or ring rolling). Thus, the inner layer may comprise the same or different material as the outer layer(s). The inner layer may also have higher or lower strength and/or abrasion resistance than the outer layers.

In one or more implementations, the inner layer is joined or bonded to the outer layer(s) of the multi-layered bag. The joining of the inner layer to the outer layer(s) can control how much the inner layer may or may not stretch in use. For instance, to allow the inner layer to stretch freely and independently from the outer layer(s), the inner layer may be joined to the outer layer along only a hem seal near the top of the layers. Alternatively or additionally, the side edges of the inner and outer layers can be joined together. To prevent at least some stretching of the inner layer, the side walls of the inner layer can be laminated to the sidewalls of the outer layer(s). To allow an intermediate amount of stretching, only intermediate or discrete portions of the sidewalls of the inner layer can be laminated to the sidewalls of the outer layer(s).

Lamination of at least a portion of the inner layer to any adjacent or outer layers can be accomplished through one or more suitable techniques. For example, bonding may be achieved by pressure only (for example ring rolling, strainable network lamination, or embossing), or with a combination of heat and pressure. Alternately, the film layers can be laminated by ultrasonic bonding. Alternately, the films can be laminated by the application of adhesives to one or more layers. Treatment with a Corona discharge can enhance any of the above methods. Prior to lamination, the separate layers can be flat film or can be subject to separate processes, such as stretching, slitting, coating and printing, and corona treatment.

In one or more implementations, the lamination between the inner layer and adjacent or outer layer(s) of a multi-layer is relatively light such that forces acting on the multi-layer film are first absorbed by breaking the lamination bonds rather than, or prior to, tearing or otherwise causing the failure of the layers of the multi-layer bag. In particular, the bonds or bond regions of an inner layer and adjacent or outer layer(s) of multi-layer bags in accordance with one or more implementations can act to first absorb forces via breaking of the bonds prior to allowing that same force to cause failure of the individual layers of the multi-layer bag. Such action can provide increased strength to the multi-layer bag. In one or more implementations, the bonds or bond regions include a bond strength that is advantageously less than a weakest tear resistance of each of the individual films so as to cause the bonds to fail prior to failing of the film layers. Indeed, one or more implementations include bonds that the release just prior to any localized tearing of the layers of the multi-layer bag. In particular, bonds formed by pressure only may have bond strengths less than the weakest tear resistance.

Thus, in one or more implementations, bonds or bond regions of a multi-layer film or bag can fail before either of the individual layers undergo molecular-level deformation. For example, an applied strain can pull the bonds or bond regions apart prior to any molecular-level deformation (stretching, tearing, puncturing, etc.) of the individual film layers. In other words, the light bonds or bond regions can provide less resistive force to an applied strain than molecular-level deformation of any of the layers of the multi-layer film or bag. The inventors have surprisingly found that such a configuration of light bonding can provide increased strength properties to the multi-layer film or bag as compared to a film or bag with a monolayer equal thickness or a multi-layer film or bag in which the plurality of layers are tightly bonded together (e.g., coextruded).

One or more implementations of the present invention provide for tailoring the bonds or bond regions between layers of a multi-layer bag in different regions of the bag. For example, one or more implementations include modifying or tailoring one or more of bond strength, bond density, bond pattern, bond type and/or bond size of different sections of a multi-layer film or bag to deliver a bag with zones or sections with tailored strength and/or aesthetic characteristics.

As used herein, the terms "lamination," "laminate," and "laminated film," refer to the process and resulting product made by bonding together two or more layers of film or other material. The term "bonding," when used in reference to bonding of multiple layers of a multi-layer film, may be used interchangeably with "lamination" of the layers. According to methods of the present invention, adjacent layers of a multi-layer film are laminated or bonded to one another. In one or more implementations, the bonding purposely results in a relatively weak bond between the layers that has a bond strength that is less than the strength of the weakest layer of the film. This allows the lamination bonds to fail before the film layer, and thus the film, fails.

The term laminate does not include heated coextruded multilayer films comprising one or more tie layers. As a verb, "laminate" means to affix or adhere (by means of, for example, adhesive bonding, pressure bonding, ultrasonic bonding, corona lamination, and the like) two or more separately made film articles to one another so as to form a multi-layer structure. As a noun, "laminate" means a product produced by the affixing or adhering just described.

The individual layers (i.e., inner and outer layers) of the multi-layer bags of one or more implementations may each themselves comprise a plurality of laminated layers. Such layers may be significantly more tightly bonded together than the bonding provided between the inner and outer layers. Both tight and relatively weak lamination can be accomplished by joining layers by mechanical pressure, joining layers with adhesives, joining with heat and pressure, joining the layers by heat, and combinations thereof. Adjacent sublayers of an individual layer may be coextruded. Coextrusion results in tight bonding so that the bond strength is generally greater than the tear resistance of the resulting layers (i.e., rather than allowing adjacent layers to be peeled apart through breakage of the coextrusion bonds, the film will tear).

In one or more implementations, the light lamination or bonding between layers of a multi-layer bag may be non-continuous (i.e., discontinuous or partial discontinuous). As used herein the terms "discontinuous bonding" or "discontinuous lamination" refers to lamination of two or more layers where the lamination is not continuous in the machine direction and not continuous in the transverse direction. More particularly, discontinuous lamination refers to lamination of two or more layers with repeating bonded patterns broken up by repeating un-bonded areas in both the machine direction and the transverse direction of the film. Or alternatively, random bonded areas broken up by random un-bonded areas.

As used herein the terms "partially discontinuous bonding" or "partially discontinuous lamination" refers to lamination of two or more layers where the lamination is substantially continuous in the machine direction or in the transverse direction, but not continuous in the other of the machine direction or the transverse direction. Alternately, partially discontinuous lamination refers to lamination of two or more layers where the lamination is substantially continuous in the width of the article but not continuous in the height of the article, or substantially continuous in the height of the article but not continuous in the width of the article. More particularly, partially discontinuous lamination refers to lamination of two or more layers with repeating bonded patterns broken up by repeating unbounded areas in either the machine direction or the transverse direction.

As used herein, the term "flexible" refers to materials that are capable of being flexed or bent, especially repeatedly, such that they are pliant and yieldable in response to externally applied forces. Accordingly, "flexible" is substantially opposite in meaning to the terms inflexible, rigid, or unyielding. Materials and structures that are flexible, therefore, may be altered in shape and structure to accommodate external forces and to conform to the shape of objects brought into contact with them without losing their integrity. In accordance with further prior art materials, web materials are provided which exhibit an "elastic-like" behavior in the direction of applied strain without the use of added traditional elastic. As used herein, the term "elastic-like" describes the behavior of web materials which when subjected to an applied strain, the web materials extend in the direction of applied strain, and when the applied strain is released the web materials return, to a degree, to their pre-strained condition.

Film Materials

As an initial matter, one or more layers of the films can comprise any flexible or pliable material comprising a thermoplastic material and that can be formed or drawn into a web or film. Each individual film layer may itself include a single layer or multiple layers. Adjuncts may also be included, as desired (e.g., pigments, slip agents, anti-block agents, tackifiers, or combinations thereof). The thermoplastic material of the films of one or more implementations can include, but are not limited to, thermoplastic polyolefins, including polyethylene, polypropylene, and copolymers thereof. Besides ethylene and propylene, exemplary copolymer olefins include, but are not limited to, ethylene vinylacetate (EVA), ethylene methyl acrylate (EMA) and ethylene acrylic acid (EAA), or blends of such olefins. Various other suitable olefins and polyolefins will be apparent to one of skill in the art.

Other examples of polymers suitable for use as films in accordance with the present invention include elastomeric polymers. Suitable elastomeric polymers may also be biodegradable or environmentally degradable. Suitable elastomeric polymers for the film include poly(ethylene-butene), poly(ethylene-hexene), poly(ethylene-octene), poly(ethylene-propylene), poly(styrene-butadiene-styrene), poly(styrene-isoprene-styrene), poly(styrene-ethylene-butylene-styrene), poly(ester-ether), poly(ether-amide), poly(ethylene-vinylacetate), poly(ethylene-methylacrylate), poly(ethylene-acrylic acid), poly(ethylene butylacrylate), polyurethane, poly(ethylene-propylene-diene), ethylene-propylene rubber, and combinations thereof.

In at least one implementation of the present invention, the film can include linear low density polyethylene. The term "linear low density polyethylene" (LLDPE) as used herein is defined to mean a copolymer of ethylene and a minor amount of an alkene containing 4 to 10 carbon atoms, having a density of from about 0.910 to about 0.926 g/cm$^3$, and a melt index (MI) of from about 0.5 to about 10. For example, one or more implementations of the present invention can use an octene co-monomer, solution phase LLDPE (MI=1.1; p=0.920). Additionally, other implementations of the present invention can use a gas phase LLDPE, which is a hexene gas phase LLDPE (MI=1.0; p=0.920). One will appreciate that the present invention is not limited to LLDPE, and can include "high density polyethylene" (HDPE), "low density polyethylene" (LDPE), and "very low density polyethylene" (VLDPE). Indeed films made from any of the previously mentioned thermoplastic materials or combinations thereof can be suitable for use with the present invention.

One will appreciate in light of the disclosure herein that manufacturers may form the individual films or webs so as to provide improved strength characteristics using a wide variety of techniques. For example, a manufacturer can form a precursor mix of the thermoplastic material including any optional additives. The manufacturer can then form the film(s) from the precursor mix using conventional flat extrusion, cast extrusion, or coextrusion to produce monolayer, bilayer, or multilayered films.

Alternative to conventional flat extrusion or cast extrusion processes, a manufacturer can form the films using other suitable processes, such as, a blown film process to produce monolayer, bilayer, or multilayered films. If desired for a given end use, the manufacturer can orient the films by trapped bubble, tenterframe, or other suitable processes. Additionally, the manufacturer can optionally anneal the films.

In one or more implementations, the films of the present invention are blown film, or cast film. Blown film and cast film is formed by extrusion. The extruder used can be a conventional one using a die, which will provide the desired gauge. Some useful extruders are described in U.S. Pat. Nos. 4,814,135; 4,857,600; 5,076,988; 5,153,382, each of which are incorporated herein by reference. Examples of various extruders, which can be used in producing the films to be used with the present invention, can be a single screw type modified with a blown film die, an air ring, and continuous take off equipment.

In one or more implementations, a manufacturer can use multiple extruders to supply different melt streams, which a feed block can order into different channels of a multi-channel die. The multiple extruders can allow a manufacturer to form a multi-layered film with layers having different compositions. In a blown film process, the die can be an upright cylinder with a circular opening. Rollers can pull molten plastic upward away from the die. An air-ring can cool the film as the film travels upwards. An air outlet can force compressed air into the center of the extruded circular profile, creating a bubble. The air can expand the extruded circular cross section by a multiple of the die diameter. This ratio is called the "blow-up ratio." When using a blown film process, the manufacturer can collapse the film to double the plies of the film. Alternatively, the manufacturer can cut and fold the film, or cut and leave the film unfolded.

Figure 2:
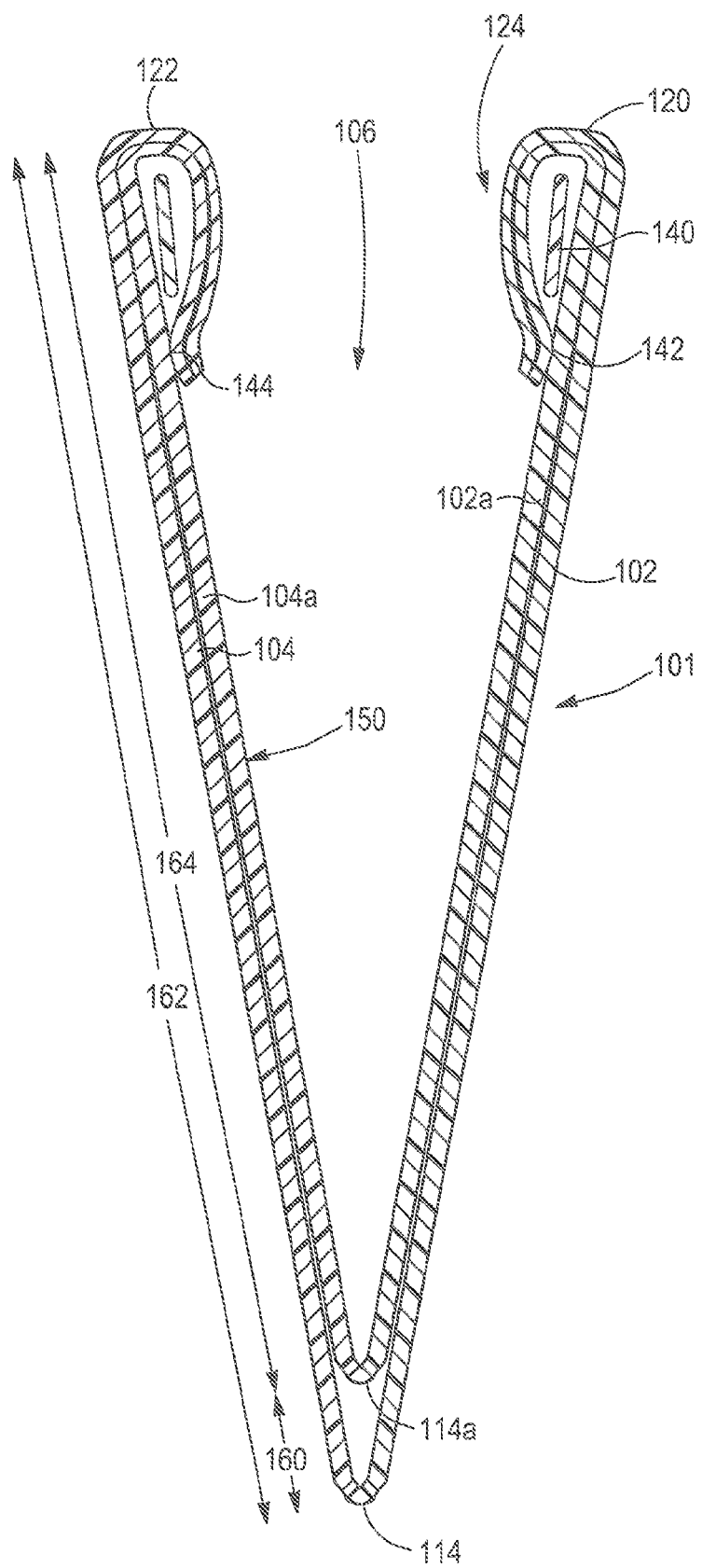
FIG. 2 illustrates a cross-sectional view of the multi-layered thermoplastic bag of FIG. 1 taken along the section line 2-2 of FIG. 1.

Referring to FIGS. 1 and 2, an implementation of multi-layered thermoplastic bag 100 with a shortened inner layer is illustrated. While the multi-layered bags of one or more implementations are generally capable of holding a vast variety of different contents, the multi-layered bag 100 illustrated in FIG. 1 may be intended to be used as a liner for a garbage can or similar refuse container. The multi-layered thermoplastic bag 100 can include a first layer or bag 101 including a first sidewall 102 and a second sidewall 104. The first and second sidewalls 102, 104 can be joined together along a first side edge 110, an opposing second side edge 112, and along a bottom edge 114. The bottom edge 114 can extend between the first and second side edges 110, 112. The first and second sidewalls 102, 104 may be joined along the first and second side edges 110, 112 and bottom edge 114 by any suitable process such as, for example, a heat seal. In one or more implementations, the bottom edge 114 or one or more of the side edges 110, 112 can comprise a fold.

To allow access to the interior volume of the multi-layered bag 100 at least a portion of the top edges 120, 122 of the first and second sidewalls 102, 104 may be un-joined to define an opening 124. The opening 124 can be opposite the bottom edge 114. When placed in a trash receptacle, the top edges 120, 122 of the first and second sidewalls 102, 104 may be folded over the rim of the receptacle.

The multi-layered bag 100 also optionally includes a closure mechanism located adjacent to the upper edges 120, 122 for sealing the top of the multi-layered bag 100 to form a fully-enclosed container or vessel. As shown by FIGS. 1 and 2, the closure mechanism can comprise a draw tape 140. To accommodate the draw tape 140 the first top edge 120 of the first sidewall 102 may be folded back into the interior volume 106 and may be attached to the interior surface of the sidewall to form a first hem 142. Similarly, the second top edge 122 of the second sidewall 104 may be folded back into the interior volume and may be attached to the second sidewall 104 to form a second hem 144.

As shown by FIG. 2, in one or more implementations, the draw tape 140 extends loosely through the first and second hems 142, 144 along the first and second top edge 120, 122. To access the draw tape 140, first and second notches 146, 148 (FIG. 1) may be disposed through the respective first and second top edges 120, 122. Pulling the draw tape 140 through the notches 146, 148 will constrict the first and second top edge 120, 122 thereby closing or reducing the opening 124. The draw tape closure may be used with any of the implementations of a reinforced thermoplastic bag described herein. One will appreciate in light of the disclosure herein that the present invention is not limited to draw tape closure mechanisms. In alternative implementations, the closure mechanism can comprise flaps, adhesive tapes, a tuck and fold closure, an interlocking closure, a slider closure, a zipper closure or other closure structures known to those skilled in the art for closing a bag.

As previously mentioned, the multi-layered bag 100 further includes a second layer or bag 150 (shown in dashes in FIG. 1). The second layer or bag 150 can include a first sidewall 102a and a second sidewall 104a. The first and second sidewalls 102a, 104a can be joined together along a first side edge 110a, an opposing second side edge 112a, and along a bottom edge 114a. The bottom edge 114a may extend between the first and second side edges 110a, 112a. The first and second sidewalls 102a, 104a may be joined along the first and second side edges 110a, 112a and bottom edge 114a by any suitable process such as, for example, a heat seal. In one or more implementations, the bottom edge 114a or one or more of the side edges 110a, 112a can comprise a fold.

As shown by FIGS. 1 and 2, the second layer or bag 150 is positioned within the first layer or bag 101. Such a configuration may be considered a "bag-in-bag" configuration. In other words the multi-layered bag 100 can include a second thermoplastic layer or bag 150 positioned within a first thermoplastic layer or bag 101. Each of the first and second layers or bags 101, 150 can include a pair of opposing sidewalls joined together along three edges as described above.

The multi-layered bag 100 can also be considered as a bag with multi-layered sidewalls. For example, the first sidewalls 102, 102a of the first and second layers or bags 101, 150 can be considered a first sidewall of the multi-layered bag 100. Similarly, the second sidewalls 104, 104a of the first and second layers or bags 101, 150 can be considered a second sidewall of the multi-layered bag 100.

Each of the sidewalls 102, 104, 102a, 104a (or in other words each of the inner and outer layers or bags 101, 150) can have a gauge or thickness (i.e., average distance between the major surfaces) between about 0.1 mils to about 10 mils, suitably from about 0.1 mils to about 4 mils, suitably in the range of about 0.1 mils to about 2 mils, suitably from about 0.1 mils to about 1.25 mils, suitably from about 0.9 mils to about 1.1 mils, suitably between about 0.2 mils to about 0.9 mils, and suitably between about 0.3 mils to about 0.7 mils. Additionally, as shown by FIG. 2, the sidewalls 102, 104 can have a thickness approximately equal to the thickness of the sidewalls 102a, 104a. In alterative implementations, the sidewalls 102, 104 may be thinner than the sidewalls 102a, 104a. In yet further implementations, the sidewalls 102, 104 may be thicker than the sidewalls 102a, 104a.

As shown in FIG. 2, each of the sidewalls 102, 104, 102a, 104a can have a uniform or consistent gauge. In alternative implementations, one or more of the sidewalls 102, 104, 102a, 104a can be rough or uneven. Further, the gauge of one or more of the sidewalls 102, 104, 102a, 104a need not be consistent or uniform. Thus, the gauge of one or more of the sidewalls 102, 104, 102a, 104a can vary due to product design, manufacturing defects, tolerances, or other processing issues.

In particular, in one or more implementations one or more of the sidewalls 102, 104, 102a, 104a is incrementally stretched as explained in greater detail below. For example, in one or more implementations one or more of the 102, 104, 102a, 104a is incrementally stretched by one or more of MD ring rolling, transverse direction TD ring rolling, SELFing, or other methods described in U.S. patent application Ser. No. 13/273,384 filed Oct. 14, 2011 and entitled NON-CONTINUOUSLY LAMINATED MULTI-LAYERED BAGS, previously incorporated by reference herein. Incrementally stretching one or more of the sidewalls 102, 104, 102a, 104a can increase or otherwise modify one or more of the tensile strength, tear resistance, impact resistance, or elasticity of the films, while also reducing the basis weight of the film.

The sidewalls 102, 104, 102a, 104a can each comprise films of thermoplastic material. In particular, the sidewalls 102, 104, 102a, 104a can comprise any of the thermoplastic materials described hereinabove, or combinations thereof. In one or more implementations, the sidewalls 102, 104 can comprise the same thermoplastic material as the sidewalls 102a, 104a. In alternative implementations, the sidewalls 102a, 104a can comprise a different thermoplastic material than the sidewalls 102, 104. For example, the material of the sidewalls 102a, 104a may have a higher tensile strength, tear resistance, puncture resistance, elasticity, and/or abrasion resistance than the material of the sidewalls 102, 104. Sidewalls 102a, 104a made of stronger and/or tougher material may help further protect the multi-layered bag 100 against rupture and/or puncture.

In at least one implementation the inner bag 150 includes an elastic material that allows the inner bag 150 to expand to the size of the outer bag 101 when filled with objects, such as trash, or otherwise strained. For example, in one or more implementations the inner bag can comprise a PLASTOMER from Dow Chemical Company, Midland, Mich., a FLEXIMER from Dow Chemical Company, Midland, Mich., ethylene propylene diene monomer, polybutylene, poly(1-butene), combinations thereof, or other materials with similar elastic characteristics. In one or more implementations the inner bag can comprise a material that has a tensile yield strength lower than the tensile yield strength of LLPDE with a density of about 0.915 to about 0.925 g/cm$^3$.

In addition to the forgoing, in one or more implementations the sidewalls 102, 104, 102a, 104a can comprise the same color. In alternative implementations, the color of the sidewalls 102a, 104a and the sidewalls 102, 104 can differ. For example, in one or more implementations the sidewalls 102, 104 can comprise a white, translucent thermoplastic material. The sidewalls 102a, 104a can comprise a pigmented (i.e., non-white) thermoplastic material. For example, in one or more implementations the sidewalls 102a, 104a can comprise a black thermoplastic material. In such implementations, the areas of the multi-layered bag 100 reinforced by the sidewalls 102a, 104a can appear gray when view from the outside of the multi-layered bag 100. Thus, the differing color of the areas of the multi-layered bag 100 reinforced by the inner layer 150 can serve to notify a consumer that such areas of the multi-layered bag 100 are reinforced. Furthermore, the difference in color can also serve to notify the consumer once the inner layer or bag 150 stretches to the size of the outer layer or bag 101, as the bottom of the outer layer or bag 101 will change from a white appearance to a grey appearance.

The individual films or layers (e.g., inner layer or bag 150 and outer layer or bag 101) may each themselves comprise a plurality of film layers. Such film layers may be joined by mechanical pressure, adhesives, heat and pressure, spread coating, extrusion coating, and combinations thereof. In particular, one or more of the sidewalls 102, 104, 102a, 104a can comprise two, three, four, or more coextruded, continuously laminated, non-continuously laminated, or otherwise bonded layers. For ease in description, the sidewalls 102, 104, 102a, 104a are described and shown herein as single film layers. One will appreciate, however, that the present invention is not so limited, and the sidewalls 102, 104, 102a, 104a can each include one, two, three, or more layers.

Additionally, as shown by FIGS. 1 and 2, the multi-layered bag 100 includes multiple layers. FIGS. 1 and 2 illustrate a multi-layered bag 100 with two layers. One will appreciate in light of the disclosure herein that in alternative implementations one or more multi-layered bags of the present invention can include more than two layers. For example, multi-layered bags of one or more implementations can include 3, 4, 5, 6, or more layers.

In any event, multi-layered bags of one or more implementations at least one inner layer that is shorter than at least one adjacent or outer layer. For example, FIGS. 1 and 2 illustrate that the multi-layered bag 100 includes a second, inner layer or bag 150 that is shorter than a first, outer layer 101. Thus, the bottom edge 114a of the second layer or bag 150 is spaced a distance 160 from the bottom edge 114 of the first layer or bag 101. Thus, the sidewalls 102, 104 the first layer or bag 101 can have a first length 162, while the sidewalls 102a, 104a of the second layer or bag 150 can have a second length 164 that is less than the first length 162. In other words, each of the sidewalls of the multi-layered bag can include outer layers 102, 104 with a first length 162 and inner layers 102a, 104a with a second length 164 that is less than the first length 162.

The length 162 may have a first range of about 20 inches (50.8 cm) to about 48 inches (121.9 cm), a second range of about 23 inches (58.4 cm) to about 33 inches (83.8 cm), and a third range of about 26 inches (66 cm) to about 28 inches (71.1 cm). In one implementation, the length 162 may be 27.375 inches (69.5 cm). In alternative implementations, the length 162 may be shorter or longer than the examples listed above.

Along similar lines, the length 164 may have a first range of about 20 inches (50.8 cm) to about 48 inches (121.9 cm), a second range of about 23 inches (58.4 cm) to about 33 inches (83.8 cm), and a third range of about 26 inches (66 cm) to about 28 inches (71.1 cm). In one implementation, the length 164 may be 27.375 inches (69.5 cm). In alternative implementations, the length 164 may be shorter or longer than the examples listed above. In any event, the length 164 may be smaller than the length 162.

In particular, as described above, the length 164 can be shorter than the length 162 by a distance 160 between the bottom edge 114a of the second layer or bag 150 and the bottom edge 114 of the first layer or bag 101. The distance 160 can vary based on the elasticity of the inner layer or bag 150 or other design factors. In one or more implementations, the distance 160 comprises between about 5% and 50% of the length 162. In alternative implementations, the distance 160 comprises about 5%, 10%, 15%, 20%, 25%, 30%, 35%, 40%, or 45% of the length 162 of the outer layer or bag 101. In alternative implementations, the distance 160 can be greater than 50% of the length 162 of the outer layer or bag 101. One will appreciate in light of the disclosure herein that the shortened inner layer or bag 150 can allow for a reduction in material as compared with a conventional bag.

In one or more implementations, the inner layer or bag 150 is joined or bonded to the outer layer or bag 101 of the multi-layered bag 100. For example, FIG. 2 illustrates that in one implementation the inner layer or bag 150 is joined to the outer layer or bag 101 only along the hems 142, 144. Thus, the inner layer or bag 150 can expand or stretch freely relative to the outer layer or bag 101. In such implementations, the inner layer or bag 150 can act independently of the outer layer or bag 101. In particular, the inner layer or bag 150 can act as a shock absorber and absorb forces associated with loading the multi-layered bag 100.

In alternative implementations, the inner layer or bag 150 can additionally, or alternatively, be joined to the outer layer or bag 101 along their respective edges. For example, one or more of the first side edges 110, 110a and the second side edges 112, 112a of the respective inner and outer layers or bags 101, 150 can be joined by a heat seal, a fold, or other mechanism. In at least one implementation the first side edges 110, 110a and the second side edges 112, 112a of the inner and outer layers or bags 101, 150 are joined by heat seals, while the bottom edges 114, 114a comprise folds that are un-joined to each other. One will appreciate in light of the disclosure herein that heat seals or other mechanisms bonding the first side edges 110, 110a and the second side edges 112, 112a of the inner and outer layers or bags 101, 150 together can restrict or prevent at least some stretching of the inner layer or bag 150.

In addition to the foregoing, in one or more implementations one or more of the sidewalls 102a, 104a of the inner layer or bag 150 can be laminated to the respective sidewalls 102, 104 of the outer layer or bag 101. For example, the sidewalls 102a, 104a of the inner layer or bag 150 can be continuously bonded to the sidewalls 102, 104 of the outer layer or bag 101. For example, the inner and outer layers or bags 101, 150 can be co-extruded, joined shortly after extrusion while still tacky, adhesively bonded, or otherwise continuously bonded.

In alternative implementations the inner layer or bag 150 is non-continuously laminated to the outer layer or bag 101. For example, the inner layer or bag 150 can be non-continuously laminated to the outer layer or bag 101 using any of the methods, process, and techniques described in previously incorporated by reference U.S. patent application Ser. No. 13/273,384 filed Oct. 14, 2011 and entitled NON-CONTINUOUSLY LAMINATED MULTI-LAYERED BAGS. For example, the inner layer or bag 150 can be non-continuously laminated to the outer layer or bag 101 using a process selected from the group consisting of adhesive bonding, ultrasonic bonding, embossing, ring rolling, SELFing, and combinations thereof.

In at least one implementation, the lamination between the inner and outer layers or bags 101, 150 can have a bond strength that is less than a weakest tear resistance of each of the inner and outer layers or bags 101, 150 so as to cause the lamination to fail prior to failing of the inner and outer layers or bags 101, 150. Indeed, one or more implementations include bonds that the release just prior to any localized tearing of the inner and outer layers or bags 101, 150. In particular, the lamination between the inner and outer layers or bags 101, 150 can act to first absorb forces via breaking of the bonds prior to allowing that same force to cause failure of the inner and outer layers or bags 101, 150. Such action can provide increased strength to the multi-layered bags of one or more implementations of the present invention.

Thus, in one or more implementations, strains applied to a multi-layered bag with a shortened inner layer can first be at least partially absorbed or softened by breaking of the bond(s) between the inner layer or bag and the outer layer or bag. Thereafter, the shortened inner bag can absorb forces and stretch to the size of the outer bag(s) before the outer bag(s) is significantly strained. Once stretched the inner bag can work in concert with the outer bag(s) to provide strength. Such implementations can provide an overall bag employing a reduced amount of raw material that nonetheless has maintained or increased strength parameters.

In addition to the foregoing, the bonds between the inner and outer layers can allow the inner layer or bag to act as a shock absorber by debonding from the outer layer or bag as articles, such as trash, are added to the bag. This debonding may allow the inner layer or bag to expand, stretch, or otherwise move downward. This debonding may also allow the inner layer or bag to separate in areas away for the added article and thus absorb some of the energy.

This is beneficial as it has been found that thermoplastic films often exhibit strength characteristics that are approximately equal to the strength of the weakest layer. Providing relatively weak bonding between the inner and outer layers or bags 101, 150 has surprisingly been found to greatly increase the strength provided by the inner layer or bag 150. As more explicitly covered in U.S. patent application Ser. No. 12/947, 025 filed Nov. 16, 2010 and entitled DISCONTINUOUSLY LAMINATED FILM, incorporated by reference herein, the MD and TD tear values of non-continuously laminated films in accordance with one or more implementations can exhibit significantly improved strength properties, despite a reduced gauge. In particular, the individual values for the Dynatup, MD tear resistance, and TD tear resistance properties in non-continuously laminated films of one or more implementations are unexpectedly higher than the sum of the individual layers. Thus, the non-continuous lamination of the inner and outer layers or bags 101, 150 can provide a synergistic effect.

More specifically, the TD tear resistance of the non-continuously laminated films can be greater than a sum of the TD tear resistance of the individual layers. Similarly, the MD tear resistance of the non-continuously laminated films can be greater than a sum of the MD tear resistance of the individual layers. Along related lines, the Dynatup peak load of the non-continuously laminated films can be greater than a sum of a Dynatup peak load of the individual layers. Thus, the non-continuously laminated films can provide a synergistic effect. In addition to the foregoing, one or more implementations of a non-continuously laminated multi-layered bag with a shortened inner layer can allow for a reduction in basis weight (gauge by weight) as much as 50% and still provide enhanced strength parameters.

Figure 3:
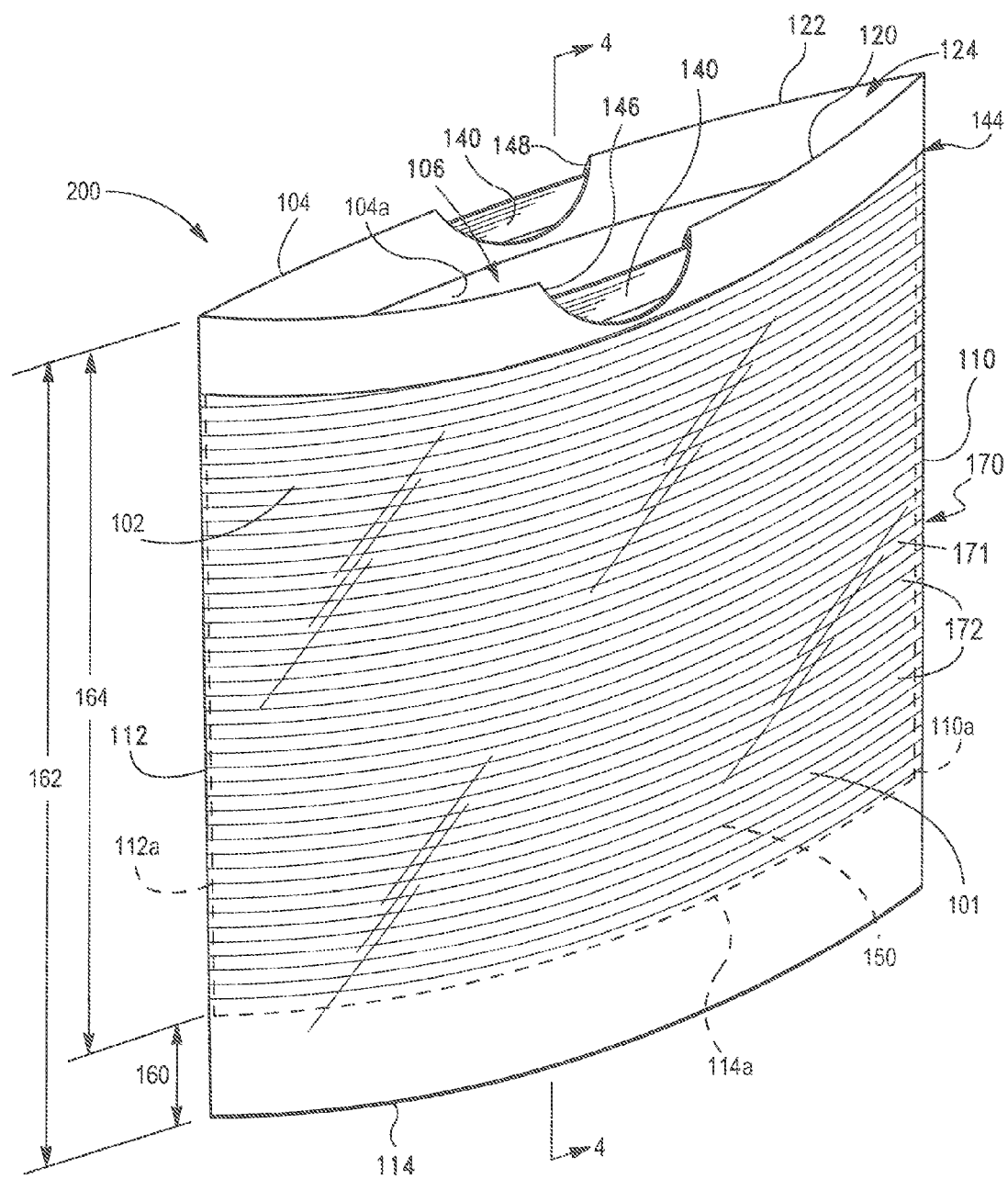
FIG. 3 illustrates a perspective view of another multi-layered thermoplastic bag with a shortened inner layer in accordance with one or more implementations of the present invention.
Figure 4:
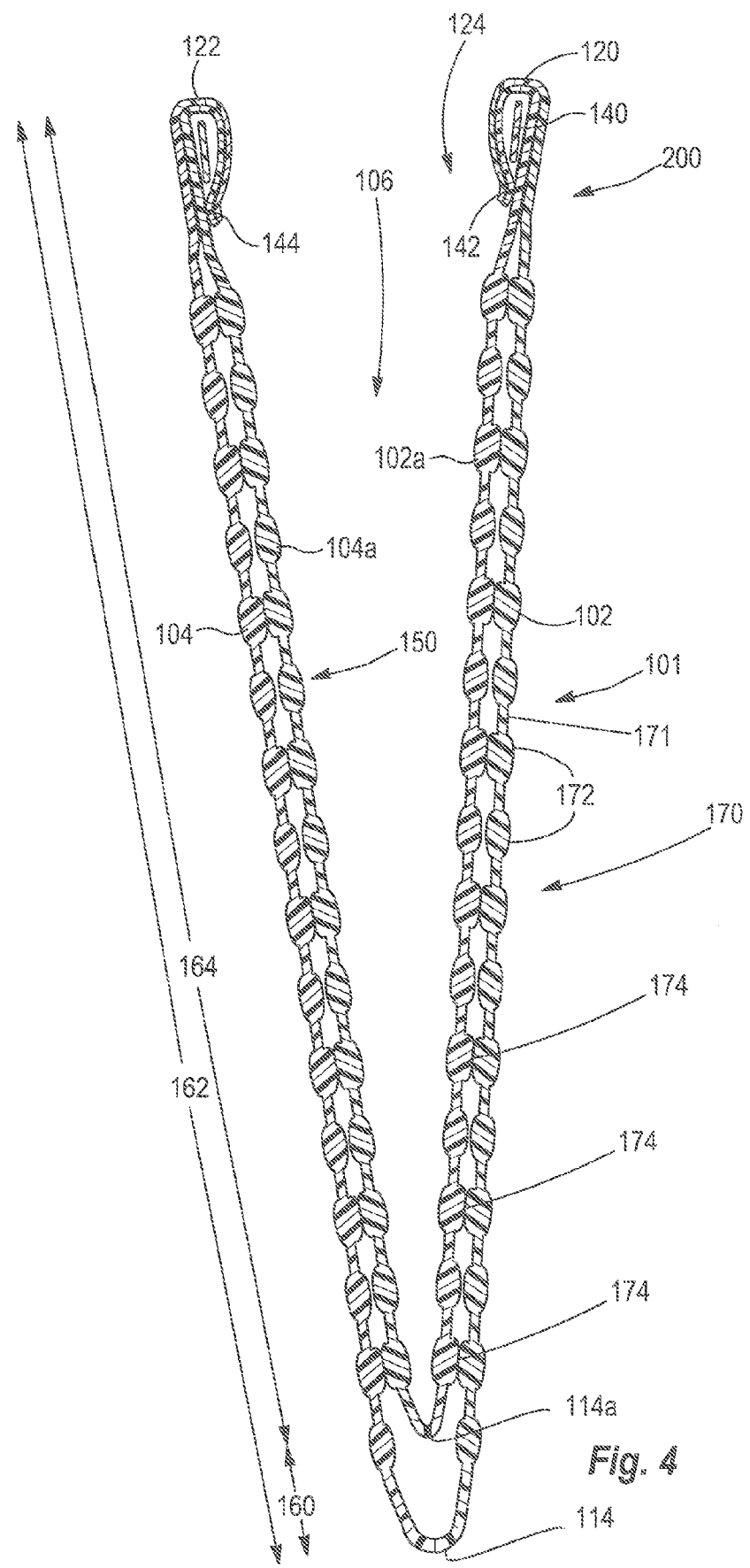
FIG. 4 illustrates a cross-sectional view of the multi-layered thermoplastic bag of FIG. 3 taken along the section line 4-4 of FIG. 1.

For example, FIGS. 3 and 4 illustrate a multi-layered bag 200 with a shortened inner layer or bag similar to the multi-layered bag 100 of FIGS. 1 and 2, albeit that the sidewalls 102a, 104a of the inner layer or bag 150 are partially discontinuously laminated to the sidewalls 102, 104 of the outer layer or bag 101. In particular, a ribbed pattern 170 can non-continuously bond the inner layer or bag 150 to the outer layer or bag 101 and provide desirable physical characteristics. The ribbed pattern 170 and associated bonds can be formed by passing the respective sidewalls 102, 102a and 104, 104a together through TD intermeshing rollers and shown and described in detail in previously incorporated by reference U.S. patent application Ser. No. 13/273,384 filed Oct. 14, 2011 and entitled NON-CONTINUOUSLY LAMINATED MULTI-LAYERED BAGS.

The ribbed pattern 170 can comprise a plurality of alternating thin linear ribs 171 and thick linear ribs 172 that may extend across the sidewall 102, 104, 102a, 104a substantially between the first side edges 110, 110a and second side edges 112, 112a. As illustrated in FIG. 3, the ribs 171, 172 may be parallel and adjacent to one another. Additionally, as illustrated in FIG. 3, the ribbed pattern 170 may extend from the bottom edge 114a toward the opening 124. To avoid interfering with the operation of the draw tape 140, the extension of the ribbed pattern 170 may terminate below the hem seals 142, 144, as illustrated by FIG. 3. In alternative implementations, the ribbed pattern 170 can extend from the bottom edge 114a to the top edges of each sidewall.

FIG. 4 further illustrates that the inner layer or bag 150 is bonded to the outer layer or bag 150. In particular, a first plurality of non-continuous bonded regions or bonds 174 can secure the first and second layers 102, 102a, 104, 104a of the each sidewall together. Thus, the bonds 174 can comprise a pattern of linear bonds 174 extending between the first side edge 110 and the second side edge 112 of each sidewall 102, 104.

As shown by FIG. 4, in one or more implementations, the bonds 174 can bond thick linear ribs 172 of the inner layer or bag 150 to thick linear ribs 172 of the outer layer or bag 101. FIG. 4 illustrates that the bonds 174 can secure some, but not all, of the thick linear ribs 172 of one layer to the thick linear ribs 172 of an adjacent layer. In particular, FIG. 4 illustrates that bonds 174 can secure every other thick linear rib 172 of adjacent layers together. In alternative implementations, bonds 174 can secure each thick linear rib 172 of adjacent layers together. Additionally, in one or more implementations the thin linear ribs 171 may be unbounded.

One will thus appreciate that the multi-layered bags with shortened inner layers can allow the inner layer or bag 150 to freely stretch by having the inner layer or bag 150 joined to the outer layer or bag 101 only along an upper hem seal. Alternatively, the multi-layered bags with shortened inner layers can prevent the inner layer or bag 150 from stretching relative to the outer layer or bag 101 by tightly bonding the layers together. In still further implementations, the multi-layered bags with shortened inner layers can allow the inner layer or bag 150 to freely stretch once relatively light non-continuous bonds between the layers are broken. In additional implementations, multi-layered bags with shortened inner layers can allow intermediate stretching of the inner layer or bag 150 by forming discrete zones of non-continuous lamination between the inner and outer layers or bags 101, 150.

Figure 5:
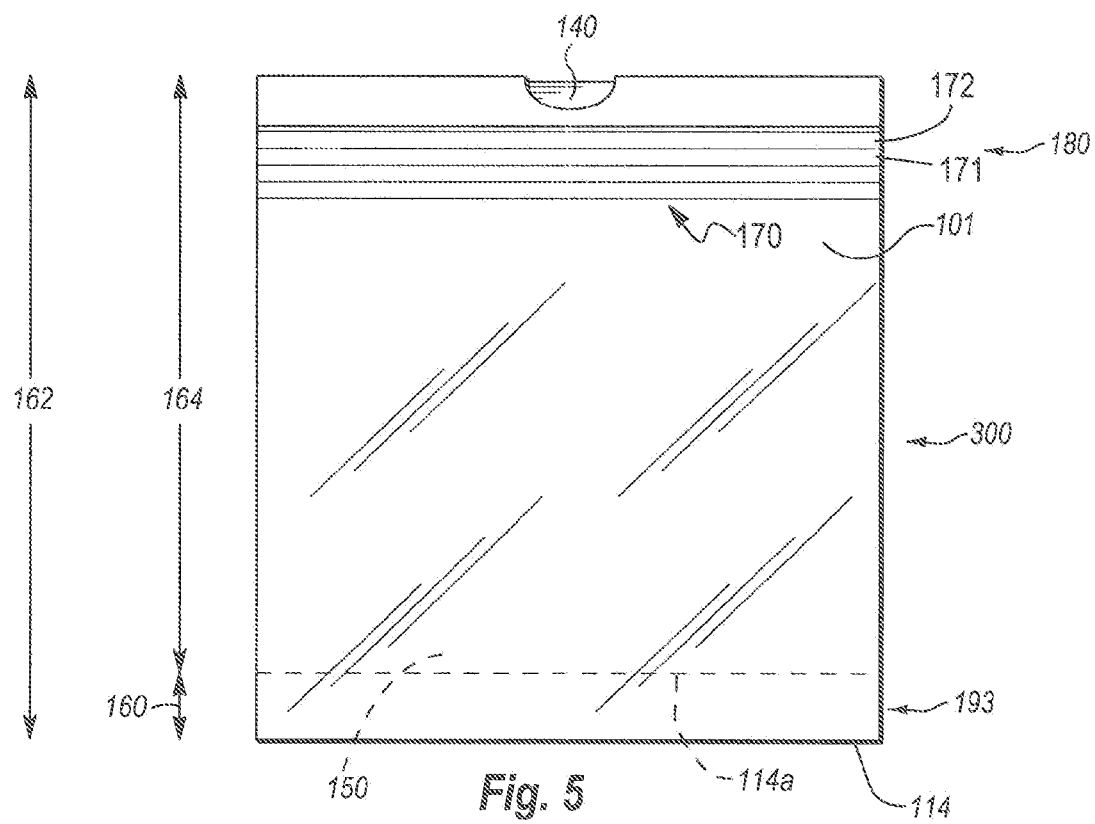
FIG. 5 illustrates a view of another multi-layered thermoplastic bag with a shortened inner layer in accordance with one or more implementations of the present invention.

For example, FIG. 5 illustrates a multi-layered bag 300 with a shortened inner layer or bag similar to the multi-layered bag 200 of FIGS. 3 and 4, albeit that the ribbed pattern 170 non-continuously bonding the inner layer or bag 150 to the outer layer or bag 101 is formed only in a top portion 180 of the bag adjacent the top of the bag 300. One will appreciate in light of the disclosure herein that the ribbed pattern 170 and associated bonds can reduce or prevent stretching (at least initially) of the top portion 180 while allowing the rest of the inner layer or bag 150 to stretch freely.

Figure 6:
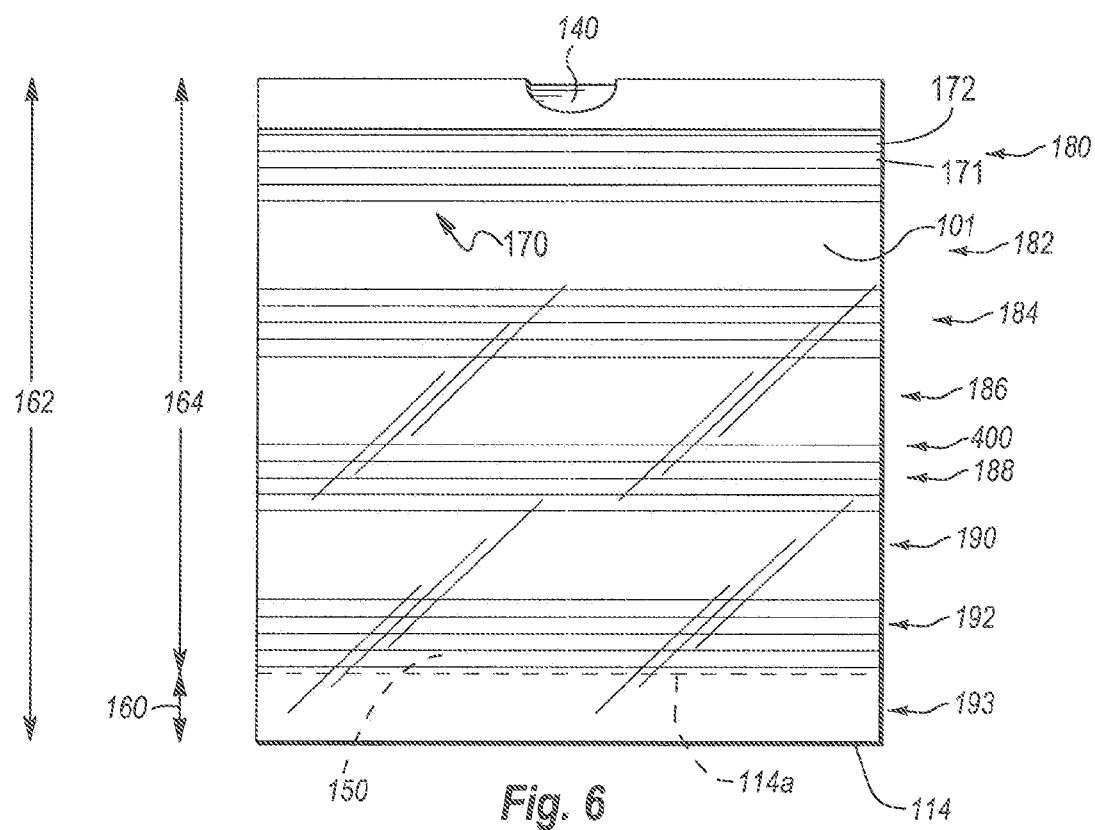
FIG. 6 illustrates a view of yet another multi-layered thermoplastic bag with a shortened inner layer in accordance with one or more implementations of the present invention.

FIG. 6 illustrates another multi-layered bag 400 with a shortened inner layer or bag. The multi-layered bag 400 can include a top portion 180, an upper-middle portion 184, a lower middle portion 186, and a bottom portion 192 with a ribbed pattern 170 non-continuously bonding the inner layer or bag 150 to the outer layer or bag 101. The portion with ribbed patterns 170 non-continuously bonding the inner layer or bag 150 to the outer layer or bag 101 are separated by portions 182, 186, 190 in which the inner layer or bag 150 is unbounded to the outer layer or bag 101.

Thus, one or more implementations allow for the tailoring of various zones or sections of a multi-layered bag with non-continuous bonds or bonded regions. In particular, different types, sizes, shapes, patterns, concentrations, and/or combinations of non-continuous bonds can provide different zones or sections of a multi-layered bag with strength and/or aesthetic properties optimal for the particular zone or section. FIG. 6 illustrates a multi-layered bag 400 with seven zones. One will appreciate that the present invention is not so limited and multi-layered bags of one or more implementations can include 0, 1, 2, 3, 4, 5, 6, or more zones or sections with tailored non-continuous bonds. Furthermore, the Figs. illustrate sections that extend along the width of the bag (i.e., bottom, middle, and upper), in alternative implementations, the sections can extend across the height of the bag (i.e., left side, middle, right side). In still further implementations the sections can comprise a combination of width-wise and length-wise extending sections. Alternatively, the sections are neither width-wise nor length-wise extending. For example, the sections can extend at an angle to the edges of the bag.

Figure 7:
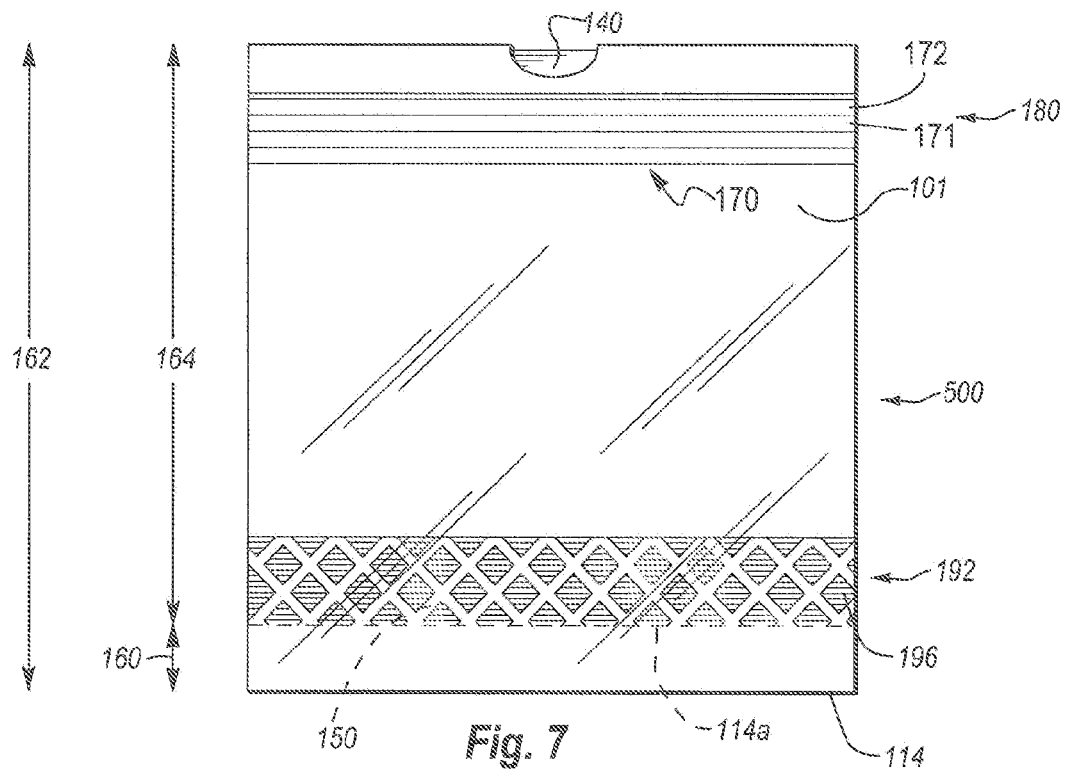
FIG. 7 illustrates a view of still another multi-layered thermoplastic bag with a shortened inner layer in accordance with one or more implementations of the present invention.

The multi-layered bags 200, 300, 400 with non-continuous bonds securing the inner layers or bags to the outer layers or bags shown in FIGS. 3-6 each include a bond pattern 170 formed by TD ring rolling. One will appreciate that the present invention is not so limited. For example, non-continuous bonds between the inner layers and outer layers or bags can be formed using any of the processes shown and described in detail in previously incorporated by reference U.S. patent application Ser. No. 13/273,384 filed Oct. 14, 2011 and entitled NON-CONTINUOUSLY LAMINATED MULTI-LAYERED BAGS. For example, FIG. 7 illustrates a multi-layered bag 500 with a shortened inner layer or bag similar to the multi-layered bag 300 of FIG. 5, albeit that the strainable network bonds 196 (i.e., bonds created by a SELFing process) arranged in diamond patterns non-continuously bond the bottom portion 192 of the inner layer or bag 150 to the outer layer or bag 101.

One will appreciate in light of the disclosure herein that the different types of non-continuous bonds in the top and bottom portions or sections 182, 192 can provide the different strength and aesthetic properties to the top and bottom sections 182, 192. For example, the non-continuous bonds created by TD ring rolling can provide the top section 182 with increased MD tear resistance, balanced MD and TD resistances, and/or increased the impact and/or puncture resistance. Additionally, the TD ring rolling of the top section 182 can result in reduced material utilization. The strainable network bonds 196 can provide the bottom section 192 with the ability to stretch around objects and prevent tears and rips. In other implementations, the inner and outer bags can be non-continuously laminated together through the use of TD ring rolling, DD, ring rolling, SELFing, ultrasonic bonding, adhesive bonding, or any combination of such various bonding techniques.

Figure 8:
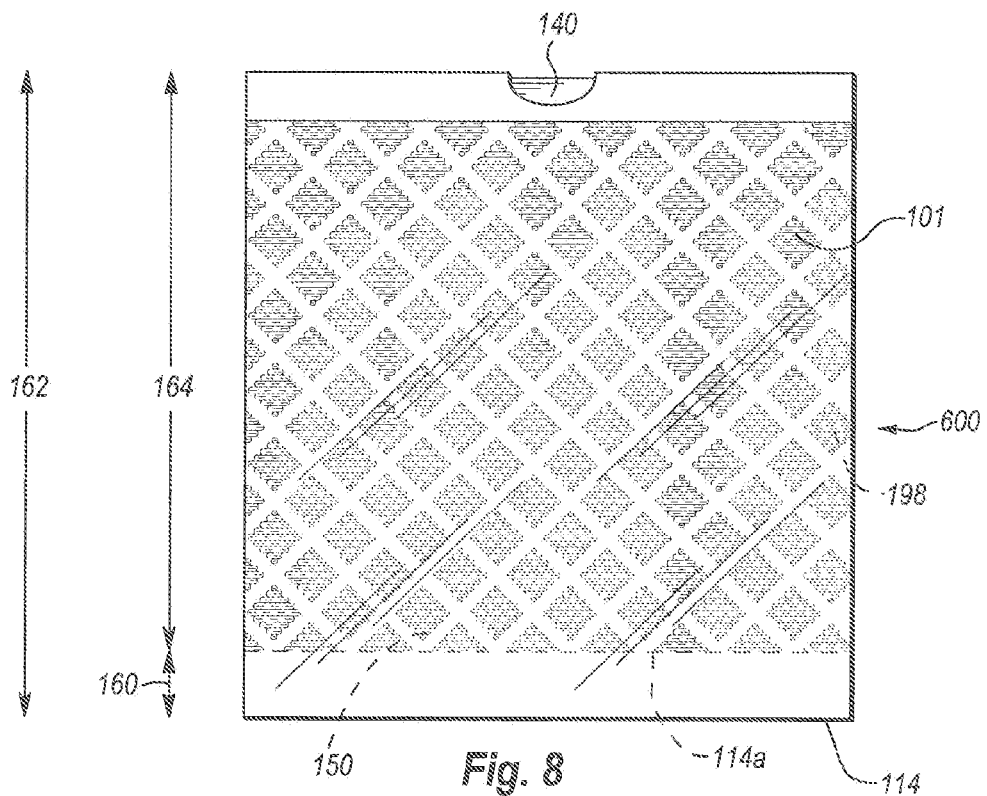
FIG. 8 illustrates a view of another multi-layered thermoplastic bag with a shortened, incrementally stretched inner layer in accordance with one or more implementations of the present invention.

In addition to non-continuous bonding, one or more layers of the multi-layered bags of one or more implementations can be incrementally stretched. One will appreciate that some types of non-continuous bonding described here can incrementally stretch the layers as they are non-continuously bonded (i.e., ring rolling, SELFing). One or more implementations of the present invention further include incrementally stretching one or more layers independent of bonding. For example, FIG. 8 illustrates a multi-layered bag 600 with a shortened inner layer or bag similar to the multi-layered bag 100 of FIGS. 1-2, albeit that the inner layer or bag 150 is incrementally stretched. In particular, the inner layer or bag 150 includes a strainable network 198 formed by a SELFing process. As shown by FIG. 8, the strainable network 198 is arranged in diamond patterns. The strainable network 198 can provide the inner layer or bag 150 with increased elasticity; thereby, allowing the inner layer or bag 150 to stretch to the size of the outer layer or bag 101 when strained.

Thus, one will appreciate in light of the disclosure herein that a manufacturer can tailor specific sections or zones of a multi-layered bag with a shortened inner layer or bag with desirable properties by MD, TD, DD ring rolling, SELF'ing, or combinations thereof. One will appreciate in light of the disclosure herein that one or more implementations can include bonded regions arranged in other patterns/shapes. Such additional patterns include, but are not limited to, intermeshing circles, squares, diamonds, hexagons, or other polygons and shapes. Additionally, one or more implementations can include bonded regions arranged in patterns that are combinations of the illustrated and described patterns/shapes.

In another implementation, a pattern may be formed by embossing, in a process similar to ring rolling. Embossed patterns such as squares, diamonds, circles or other shapes may be embossed into a multi-layer bag. The embossed, laminated film layers may be prepared by any suitable means by utilizing two or more layers of preformed web of film and passing them between embossing rollers. The method of embossing multiple layers of film can involve calendar embossing two or more separate, non-laminated layers with discrete "icons" to form bonded areas or icons, each icon having a bonded length and separated from adjacent icons by an equivalent un-bonded length. Such icons may be any desired design or shape, such as a heart, square, triangle, diamond, trapezoid, or circle.

As mentioned previously, numerous methods can be used to provide the desired degree of lamination in the bonded areas. Any of the described ring rolling techniques may be combined with other techniques in order to further increase the strength of the lamination bond while maintaining bond strength below the strength of the weakest layer of the multi-layer film. For example, heat, pressure, ultrasonic bonding, corona treatment, or coating (e.g., printing) with adhesives may be employed. Treatment with a corona discharge can enhance any of the above methods by increasing the tackiness of the film surface so as to provide a stronger lamination bond, but which is still weaker than the tear resistance of the individual layers.

Adjusting (e.g., increasing) the strength of the relatively light lamination bonding could be achieved by addition of a tackifier or adhesive to one or more of the skin plies of a multi-layer film, or by incorporating such a component into the material from which the film layer is formed. For example, the outer skin sublayers of a given layer could contain from about 0 to about 50% of a polyolefin plastomer tackifier such as a $C_4$-$C_{10}$ olefin to adjust bonding strength by increasing the tackiness of the surfaces of adjacent layers to be lightly laminated.

In one or more implementations, a component may be included to decrease tackiness. For example, the outer skin sublayers could contain higher levels of slip or anti-block agents, such as oleamide (amide of oleic acid) or talc, to decrease tack. Similarly, these surfaces may include very low levels of or be substantially void of slip or anti-block agents to provide a relative increase in tackiness.

Implementations of the present invention can also include methods of forming multi-layered lightly-laminated film and bags including the same. FIGS. 9-12 and the accompanying description describe such methods. Of course, as a preliminary matter, one of ordinary skill in the art will recognize that the methods explained in detail herein can be modified. For example, various acts of the method described can be omitted or expanded, additional acts can be included, and the order of the various acts of the method described can be altered as desired.

To produce a bag having a ribbed pattern as described, continuous webs of thermoplastic material may be processed through a high-speed manufacturing environment such as that illustrated in FIG. 9. In the illustrated process 200, production may begin by unwinding a first continuous web or film 101 of thermoplastic sheet material from a roll 202 and advancing the web along a machine direction 206. The unwound web 101 may have a width 203 that may be perpendicular to the machine direction 206, as measured between a first edge 203 and an opposite second edge 203. The first thermoplastic film 101 may have an initial average thickness measured between a first surface 209 and a second surface 211. In other manufacturing environments, the film 101 may be provided in other forms or even extruded directly from a thermoplastic forming process.

The process 200 can also involve unwinding a second continuous web or film 150 of thermoplastic sheet material from a roll 204 and advancing the web along a machine direction 206. The second film 150 can comprise a thermoplastic material and/or a thickness that is similar or the same as the first film 101. In alternative one or more implementations, one or more of the thermoplastic material and/or thickness of the second film 150 can differ from that of the first film 101. As shown in FIG. 9, the width 208 of the second film 150 can be less than the width 203 of the first film 101. One will appreciate in light of the disclosure herein that this can provide a finished multi-layered bag with a shortened inner layer or bag as shown and described herein above.

To provide the first and second sidewalls of the finished bag, the webs 101, 150 may be folded into a first half 222 and an opposing second half 224 about the machine direction 206 (i.e., along the width of the films 101, 150) by a folding operation 220. When so folded, the first edge 210 may be moved adjacent to the second edge 212 of the web. Accordingly, the width of the webs 101, 150 proceeding in the machine direction 206 after the folding operation 220 may be a width 228 that may be half the initial width 208. As may be appreciated, the portion mid-width of the unwound webs 101, 150 may become the outer edge of the folded web. In any event, the hems may be formed along the adjacent first and second edges 210, 212 and the draw tape 232 may be inserted during a hem and draw tape operation 230.

To produce the finished bag, the processing equipment may further process the folded web. For example, to form the parallel side edges of the finished bag, the web may proceed through a sealing operation 270 in which heat seals 272 may be formed between the outer edge 226 and the adjacent edges 210, 212. The heat seals may fuse together the adjacent halves 222, 224 of the folded web. The heat seals 272 may be spaced apart along the folded web and in conjunction with the folded outer edge 226 may define individual bags. The heat seals may be made with a heating device, such as, a heated knife. A perforating operation 280 may perforate 282 the heat seals 272 with a perforating device, such as, a perforating knife so that individual bags 290 may be separated from the web. In one or more implementations, the webs may be folded one or more times before the folded webs may be directed through the perforating operation. The webs 101, 150 embodying the finished multi-layered bags 284 may be wound into a roll 286 for packaging and distribution. For example, the roll 286 may be placed in a box or a bag for sale to a customer.

In one or more implementations of the process which is illustrated in FIG. 10, a cutting operation 288 may replace the perforating operation 280 in FIG. 9. Referring to FIG. 10, the web are directed through a cutting operation 288 which cuts the webs at location 290 into individual bags 292 prior to winding onto a roll 294 for packaging and distribution. For example, the roll 294 may be placed in a box or bag for sale to a customer. The bags may be interleaved prior to winding into the roll 294. In one or more implementations, the web may be folded one or more times before the folded web is cut into individual bags. In one or more implementations, the bags 292 may be positioned in a box or bag, and not onto the roll 294. The bags may be interleaved prior to positioning in the box or bag. These manufacturing implementations may be used with any of the manufacturing implementations described herein, as appropriate.

FIG. 11 illustrates another manufacturing process 200a for producing a multi-layered bag in accordance with one or more implementations of the present invention. The process 200a can be similar to process 200 of FIG. 11, except that the inner layer or film 150 can be non-continuously laminated to the outer layer 101. To impart the ribbed pattern 170 (and optionally the bonds 174), the processing equipment may include TD intermeshing rollers 242, 243 such as those described herein above. Referring to FIG. 11, the folded webs 101, 150 may be advanced along the machine direction 206 between the TD intermeshing rollers 242, 243, which may be set into rotation in opposite rotational directions to impart the resulting web pattern 150. To facilitate patterning of the webs 101, 150, the first roller 242 and second roller 243 may be forced or directed against each other by, for example, hydraulic actuators. The pressure at which the rollers are pressed together may be in a first range from 30 PSI (2.04 atm) to 100 PSI (6.8 atm), a second range from 60 PSI (4.08 atm) to 90 PSI (6.12 atm), and a third range from 75 PSI (5.10 atm) to 85 PSI (5.78 atm). In one or more implementations, the pressure may be about 80 PSI (5.44 atm).

In the illustrated implementation, the TD intermeshing rollers 242, 243 may be arranged so that they are co-extensive with or wider than the width 208 of the folded webs 101, 150. In one or more implementations, the TD intermeshing rollers 242, 243 may extend from proximate the outer edge 226 to the adjacent edges 210, 212. To avert imparting the ribbed pattern 170 onto the portion of the web that includes the draw tape 232, the corresponding ends 249 of the rollers 242, 243 may be smooth and without the ridges and grooves. Thus, the adjacent edges 210, 212 and the corresponding portion of the web proximate those edges that pass between the smooth ends 249 of the rollers 242, 243 may not be ribbed.

In one or more implementations, the webs 101, 150 may be stretched to reduce their thickness as they passes between the rollers. Referring to FIG. 11, the webs 101, 150, when unwound from the rolls 202, 204, may have an average thickness 260, measured between the first surface 216 and a second surface 218. After passing between the TD intermeshing rollers 242, 243, the web may have an average thickness that is reduced.

One result of reducing the thickness of the web material is that the ribbed pattern 170 may be imparted into the web(s) 101, 150. The thermoplastic material of the web may be stretched or worked during reduction such that the initially planar web takes the new ribbed shape. In some implementations, the molecular structure of the thermoplastic material may be rearranged to provide this shape memory. Furthermore, upon stretching, individual initially separate layers of the thermoplastic material of the web become non-continuously laminated together at, or proximate, the location of the ribs 172. In other words, at or adjacent the ribs 172, the adjacent layers 101, 150 are lightly bonded to one another, while adjacent portions are not bonded to one another.

Referring to FIG. 11, another result of reducing the web thickness is that some of the web material may be stretched longitudinally along the TD intermeshing rollers 242, 243 and perpendicular to the machine direction 206. Also, some of the web material may be compressed longitudinally along the TD intermeshing rollers 242, 243. This action may widen the folded web from its initial width 228 to a larger width 258. To facilitate the widening of the web, the adjacent edges 210, 212 of the web may be located between the smooth ends 249 of the TD intermeshing rollers 242, 243. The smooth ends 249 of the TD intermeshing rollers 242, 243 can maintain alignment of the web along the machine direction. The processing equipment may include pinch rollers 262, 264 to accommodate the growing width of the widening web.

The processed web may have varying thickness as measured along its width perpendicular of the machine direction. Because the ridges 246, 245 and the grooves 250, 251 on the TD intermeshing rollers 242, 243 may not be co-extensive with the width 228 of the folded webs 101, 150 only the thickness of that portion of the web which is directed between the ridges and the grooves may be reduced. The remaining portion of the web, such as, toward the adjacent edge 210, 212, may retain the web's original thickness. The smooth ends 249 of the TD intermeshing rollers 242, 243 may have diameters dimensioned to accommodate the thickness of that portion of the web which passes there between.

In alternative implementations, the film layers 101, 150 may pass through the TD intermeshing rollers 242, 243 prior to the folding process 220. Furthermore, the TD intermeshing rollers 242, 243 can include smooth portions 249 on each end. In alternative implementations, the TD intermeshing rollers 242, 243 can include smooth portions 249 in the middle of the rollers or intermittent smooth portions.

In still further implementations, the TD intermeshing rollers 242, 243 can be replaced with other intermeshing rollers, such as MD or DD intermeshing rollers, embossing rollers, SELFing rollers, or hybrid rollers combining one of the aforementioned types of rollers. Additionally, or alternatively, the process can include an ultrasonic horn or adhesive applicator that can bond the film layers 101, 150 together. In still further implementations, one or more of the film layers 101, 150 may pass through the intermeshing rollers or be otherwise stretched just after being unwound.

Figure 12:
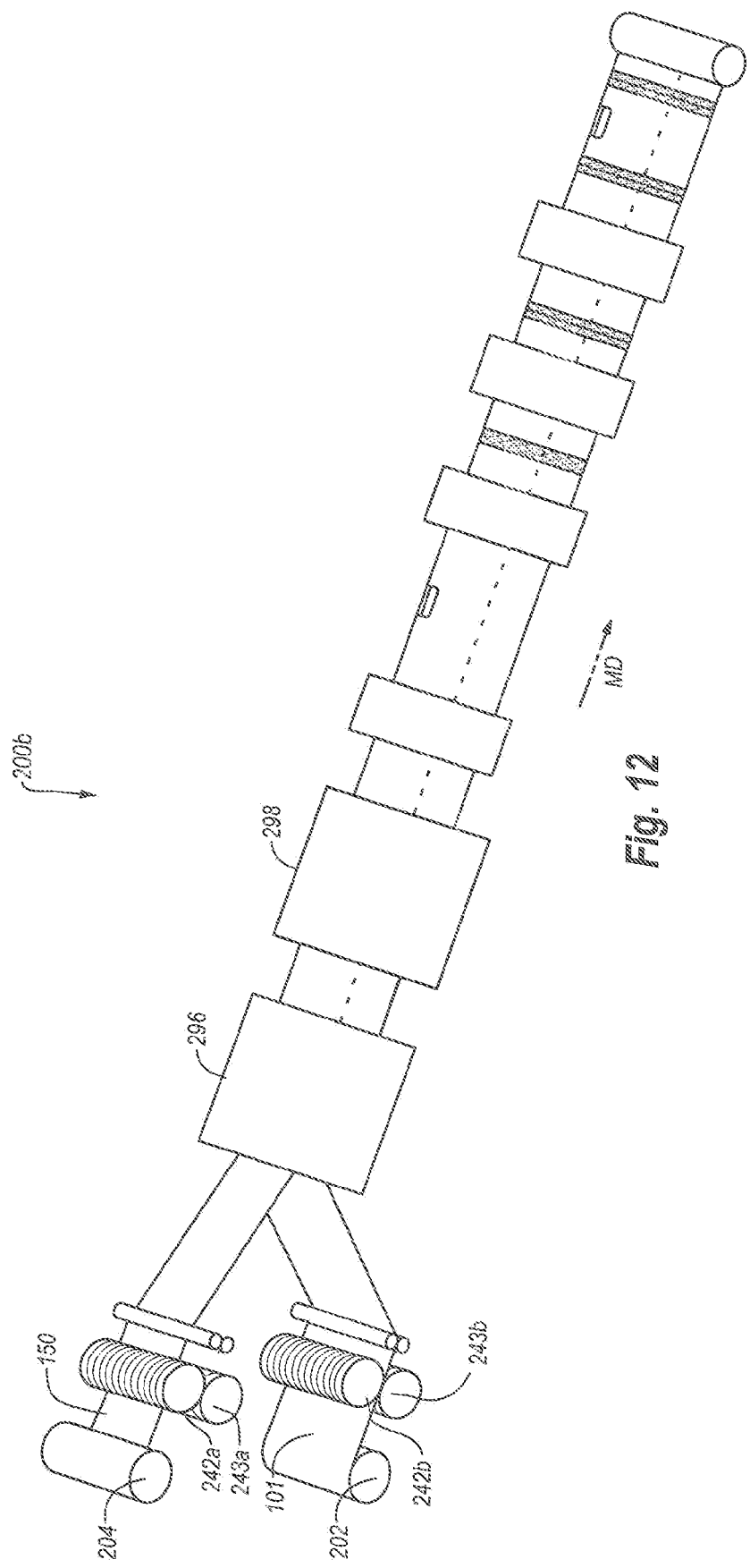
FIG. 12 illustrates a schematic view depicting yet another high-speed manufacturing process for producing multi-layered thermoplastic bags having shortened inner layers in accordance with one or more implementations of the present invention.

FIG. 12 illustrates another manufacturing process 200b for producing a multi-layered bag with a shortened inner layer or bag. The process 200b can be similar to process 200 of FIG. 11, except that the film layers 101, 150 are folded in half to form c-, u-, or j-folded films prior to winding on the rolls 202, 204. Thus, in such implementations, the films 101, 150 unwound from the rolls 202, 204 are already folded.

Additionally, the manufacturing process 200b illustrates that each film 101, 150 can pass through a set of TD intermeshing rollers 242a, 243a, 242b, 243b to incrementally stretch the films (and impart a ribbed pattern thereto) prior to bonding, or to impart one or more desired characteristics (such as elasticity). The manufacturing process 200b can then include an insertion operation 296 for inserting the folded film 101 into the folded film 150. Insertion operation 296 can combine the folded films 101, 150 using any of the apparatus and methods described in U.S. patent application Ser. No. 13/225,757 filed Sep. 6, 2011 and entitled METHID FOR INSERTING A FIRST FOLDED FILM WITHIN A SECOND FOLDED FILM and Ser. No. 13/225,930 filed Sep. 6, 2011 and entitled APPARATUS FOR INSERTING A FIRST FOLDED FILM WITHIN A SECOND C-FOLDED FILM, each of which are incorporated herein by reference in their entirety.

Additionally, FIG. 12 illustrates that the film layers 101, 150 can then pass through a lamination operation 298 to lightly bond or laminate the films 101, 150 together. Lamination operation 298 can lightly laminate the folded films 101, 150 together via adhesive bonding, pressure bonding, ultrasonic bonding, corona lamination, and the like. Alternatively, lamination operation 298 can lightly laminate the folded films 101, 150 together by passing them through machine-direction ring rolls, transverse-direction ring rolls, diagonal-direction ring rolls, SELF'ing rollers, embossing rollers, or other intermeshing rollers.

The present invention may be embodied in other specific forms without departing from its spirit or essential characteristics. Thus, the described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

We claim:

1. A multi-layered thermoplastic bag with a shortened inner layer, comprising:
    a first continuous thermoplastic bag comprising first and second opposing sidewalls joined together along a first side edge, an opposite second side edge, and a bottom edge, wherein the first and second sidewalls are un-joined to each other along at least a portion of their respective top edges to define an opening; and
    a second continuous thermoplastic bag positioned within the first thermoplastic bag, the second thermoplastic bag comprising third and fourth opposing sidewalls joined together along a first side edge, an opposite second side edge, and a bottom edge, wherein the third and fourth sidewalls are un-joined to each other along at least a portion of their respective top edges to define an opening;
    wherein the top terminal edges of the first and third sidewalls are attached together and the top terminal edges of the second and fourth sidewalls are attached together;
    wherein the second thermoplastic bag is shorter than the first thermoplastic bag such that the bottom edge of the second thermoplastic bag is spaced a distance from the bottom edge of the first thermoplastic bag, the distance being between 5% and 35% of a length of the first and second sidewalls
    wherein the second thermoplastic bag comprises an elastic material that allows the second thermoplastic bag to expand toward the first thermoplastic bag when filled with objects or otherwise strained.

2. The thermoplastic bag as recited in claim 1, wherein the first thermoplastic bag is joined to the second thermoplastic bag only along one or more hem seals proximate the top edges of the first and second thermoplastic bags.

3. The thermoplastic bag as recited in claim 1, wherein the first and second side edges of the first thermoplastic bag are joined to the first and second side edges of the second thermoplastic bag.

4. The thermoplastic bag as recited in claim 3, further comprising:
    heat seals that join the first and second side edges of the first thermoplastic bag are joined to the first and second side edges of the second thermoplastic bag; and
    wherein the bottom edges of the first and second thermoplastic bags comprise folds.

5. The thermoplastic bag as recited in claim 1, wherein each of the first and second thermoplastic bags is incrementally stretched thereby defining a ribbed pattern comprising a plurality of alternating thick and thin linear ribs.

6. The thermoplastic bag as recited in claim 5, wherein second thermoplastic bag includes a strainable network.

7. The thermoplastic bag as recited in claim 1, further comprising a plurality of non-continuous bonds securing the second thermoplastic bag to the first thermoplastic bag, the non-continuous bonds directly securing thick linear ribs of the first thermoplastic bag to thick linear ribs of the second thermoplastic bag.

8. The thermoplastic bag as recited in claim 7, wherein the plurality of non-continuous bonds are formed by one or more of embossing, ring rolling, SELFing, ultrasonic bonding, adhesive, or combinations thereof.

9. The thermoplastic bag as recited in claim 1, wherein:
    the first thermoplastic bag comprises a first color; and
    the second thermoplastic bag comprise a second color differing from the first color.

10. The thermoplastic bag as recited in claim 1, wherein the elastic material and a size of the second thermoplastic bag allow the second thermoplastic bag to absorb forces associated with loading the multi-layered bag.

11. The thermoplastic bag as recited in claim 10, further comprising a plurality of non-continuous bonds securing the first and second thermoplastic bags together, the plurality of non-continuous bonds being positioned between the top edges and the bottom edges of the first and second thermoplastic bags.

12. The thermoplastic bag as recited in claim 11, wherein a strength of the plurality of non-continuous bonds is weaker than a tear resistance of the first thermoplastic bag and a tear resistance of the second thermoplastic bag.

13. The thermoplastic bag as recited in claim 1, wherein a bottom portion of the second thermoplastic bag comprises a stretched region that allows the second thermoplastic bag to expand toward the first thermoplastic bag when filled with objects or otherwise strained.

14. A multi-layered bag, comprising:
    a first sidewall comprising a first continuous layer of a thermoplastic material and an adjacent second continuous layer of thermoplastic material;

a second sidewall comprising a first continuous layer of a thermoplastic material and an adjacent second continuous layer of thermoplastic material, wherein:

the first layers of the first and second sidewalls each have a first length;

the second layers of the first and second sidewalls each have a second length that is less than the first length, the second length being between 75% and 95% of the of the first length;

the second sidewall is joined to the first sidewall along a first side edge, an opposing second side edge, and a bottom edge, and at least a portion of respective top edges of the first and second sidewalls define an opening of the multi-layered bag; and a first plurality of non-continuous bonds securing the first and second layers of the second sidewall together, the first plurality of non-continuous bonds being positioned between the top edges and the bottom edge of the first sidewall, wherein the first plurality of non-continuous bonds have a tailored bond strength configured to allow the first plurality of non-continuous bonds to de-bond and absorb energy and allow the first and second layers delaminate when articles are added to the multi-layered bag.

15. The multi-layered bag as recited in claim 14, further comprising a second plurality of non-continuous bonds securing at least one section of the first and second layers of the first sidewall together.

16. The multi-layered bag as recited in claim 15, a third plurality of non-continuous bonds securing at least another section of the first and second layers of the first sidewall together.

17. The multi-layered bag as recited in claim 16, wherein the second plurality of non-continuous bonds differs in one or more of type or pattern from the third plurality of non-continuous bonds.

18. The multi-layered bag as recited in claim 17, wherein:
the third plurality of non-continuous bonds comprise one of ultrasonic bonds, adhesive bonds, bonds formed from MD ring rolling, bonds formed from TD ring rolling, bonds formed from embossing, or bonds formed from SELFing; and the second plurality of non-continuous bonds comprise another of ultrasonic bonds, adhesive bonds, bonds formed from MD ring rolling, bonds formed from TD ring rolling, bonds formed from embossing, or bonds formed from SELFing.

19. The multi-layered bag as recited in claim 14, further comprising at least an additional portion of the second layer of the first sidewall positioned between a first portion of the second layer bonded to the first layer by the second plurality of non-continuous bonds and a second portion of the second layer bonded to the first layer by the third plurality of non-continuous bonds, the at least another portion being un-bonded to the first layer of the first sidewall.

20. A multi-layered thermoplastic bag with a shortened inner layer, comprising:

a first continuous thermoplastic bag comprising first and second opposing sidewalls joined together along a first side edge, an opposite second side edge, and a bottom edge, wherein the first and second sidewalls are un-joined to each other along at least a portion of their respective top edges to define an opening; and a second continuous thermoplastic bag positioned within the first thermoplastic bag, the second thermoplastic bag comprising third and fourth opposing sidewalls joined together along a first side edge, an opposite second side edge, and a bottom edge, wherein the third and fourth sidewalls are un-joined to each other along at least a portion of their respective top edges to define an opening;

wherein the top terminal edges of the first and third sidewalls are attached together and the top terminal edges of the second and fourth sidewalls are attached together;

wherein the second thermoplastic bag is shorter than the first thermoplastic bag such that the bottom edge of the second thermoplastic bag is spaced a distance from the bottom edge of the first thermoplastic bag, the distance being between 5% and 35% of a length of the first and second sidewalls;

wherein a bottom portion of the second thermoplastic bag comprises a stretched region that allows the second thermoplastic bag to expand toward the first thermoplastic bag when filled with objects or otherwise strained.

* * * * *